US007371521B2

(12) United States Patent
Andersson et al.

(10) Patent No.: US 7,371,521 B2
(45) Date of Patent: May 13, 2008

(54) METHODS

(75) Inventors: Leif Andersson, Uppsala (SE); Elisabetta Giuffra, Zoagli (GE) (IT); Graham Stuart Plastow, Shipdham (GB); Olwen Irene Southwood, Wantage (GB)

(73) Assignee: Pig Improvement Company UK, Limited, Oxon (GB)

( * ) Notice: Subject to any disclaimer, the term of this patent is extended or adjusted under 35 U.S.C. 154(b) by 434 days.

(21) Appl. No.: 10/475,757

(22) PCT Filed: Apr. 24, 2002

(86) PCT No.: PCT/GB02/01875

§ 371 (c)(1),
(2), (4) Date: Jul. 26, 2004

(87) PCT Pub. No.: WO02/086158

PCT Pub. Date: Oct. 31, 2002

(65) Prior Publication Data

US 2004/0241676 A1 Dec. 2, 2004

(30) Foreign Application Priority Data

Apr. 24, 2001 (GB) ................. 0110036.1

(51) Int. Cl.
*C12Q 1/68* (2006.01)
(52) U.S. Cl. .................. 435/6; 435/91.1; 435/91.2
(58) Field of Classification Search ............. None
See application file for complete search history.

(56) References Cited

FOREIGN PATENT DOCUMENTS

| WO | WO 92/18651 | * | 10/1992 |
|---|---|---|---|
| WO | WO 97/05278 | * | 2/1997 |
| WO | WO 98/54360 | | 12/1998 |
| WO | WO 99/20795 | | 4/1999 |
| WO | WO 9920795 | * | 4/1999 |

OTHER PUBLICATIONS

Johansson et al., "The Gene for Dominant White Color in the Pig Is Closely Linked to ALB and PDGFRA on Chromosome 8," Genomics 14, 965-969 (1992), Academic Press, Inc.
Chabot et al., "The proto-oncogene c-kit encoding a transmembrane tyrosine kinase receptor maps to the mouse W locus," Nature, vol. 335, Sep. 1988, pp. 88-89.
Geissler et al., "The Dominant-White Spotting (W) Locus of the Mouse Encodes the c-kit Proto-Oncogene," Cell, vol. 55, pp. 185-192, Oct. 7, 1988, Cell Press.
Fleischman et al., "Deletion of the c-kit protooncogene in the human developmental defect piebald trait," Proc. Natl. Acad. Sci. USA, vol. 88, pp. 10885-10889, Dec. 1991.
Giebel et al., "Mutation of the KIT (mast/stem cell growth factor receptor) protooncogene in human piebaldism," Proc. Natl. Acad. Sci. USA, vol. 88, pp. 8696-8699, Oct. 1991.

Hubbard et al., "Crystal structure of the tyrosine kinase domain of the human insulin receptor," Nature, vol. 372, Dec. 22/29, 1994, pp. 746-754.
Ronaghi et al., "A Sequencing Method Based on Real-Time Pyrophosphate," Science, vol. 281, Jul. 17, 1998, pp. 363-365.
Laan et al., "Solid-phase minisequencing confirmed by FISH analysis in determination of gene copy number," Hum. Genet. (1995) 96:275-280, Springer-Verlag.
Olsson et al., "Determination of the frequencies of ten allelic variants of the Wilson disease gene (ATP7B), in pooled DNA samples," European Journal of Human Genetics (2000) 8, 933-938, Macmillan Publishers Ltd.
Ellegren et al., "Assignment of 20 Microsatellite Markers to the Porcine Linkage Map," Genomics 16, 431-439 (1993), Academic Press, Inc.
Coppieters et al., "Characterization of porcine polymorphic microsatellite loci," Animal Genetics, 1993, 24. 163-170.
Rohrer et al., "A Microsatellite Linkage Map of the Porcine Genome," Genetics 136: 231-245 (Jan. 1994), Genetics Society of America.
Gokkel et al., "Structural organization of the murine c-kit protooncogene," Oncogene (1992) 7: 1423-1429, Macmillan Press, Inc.
Giebel et al., "Organization and nucleotide sequence of the human KIT (mast/stem cell growth factor receptor) proto-oncogene," Oncogene (1992) 7: 2207-2217, Macmillan Press, Inc.
Besmer et al., "A new acute transforming feline retrovirus and relationship of its oncogene v-kit with the protein kinase gene family," Nature, vol. 320, Apr. 3, 1986, pp. 415-421.
Spritz et al., "A YAC Contig Spanning a Cluster of Human Type III Receptor Protein Tyrosine Kinase Genes (PDGFRA-KIT-KDR) in Chromosome Segment 4q12," Genomics 22, 431-436 (1994), Academic Press, Inc.
Mariani et al., "The Extension Coat Color Locus and the Loci for Blood Group O and Tyrosine Aminotransferase Are on Pig Chromosome 6," Journal of Heredity, 1996; 87:272-276.
Kijas et al., "Melanocortin Receptor 1 (MC1R) Mutations and Coat Color in Pigs," Genetics 150: 1177-1185 (Nov. 1998), Genetics Society of America.
Legault, "Genetics of Colour Variation," The Genetics of the Pig, 1998, pp. 51-69, CAB International.
Ohta, "How Gene Families Evolve," Theoretical Population Biology 37: 213-219 (1990), Academic Press, Inc.
Neitz et al., "Numbers and Ratios of Visual Pigment Genes for Normal Red-Green Color Vision," Science, vol. 267, Feb. 17, 1995, pp. 1013-1016.
Jackson, "Molecular and Developmental Genetics of Mouse Coat Color, " Annu. Rev. Genet. 1994, 28:189-217, Annual Reviews, Inc.
Claesson-Welsh et al., "cDNA cloning and expression of the human A-type platelet-derived growth factor (PDGF) receptor establishes structural similarity to the B-type PDGF receptor," Proc. Natl. Acad. Sci., vol. 86, pp. 4917-4921, Jul. 1989.

(Continued)

*Primary Examiner*—Gary Benzion
*Assistant Examiner*—Heather Calamita
(74) *Attorney, Agent, or Firm*—Hunton & Williams LLP

(57) ABSTRACT

Methods for determining the KIT genotype of pigs are provided. These methods are useful in determining coat colour genotype, breed determination and for screening pigs to determine those likely to produce larger litters, and/or those less likely to produce large litters. Kits for use in such methods are also provided.

20 Claims, 12 Drawing Sheets

OTHER PUBLICATIONS

Figure 1:
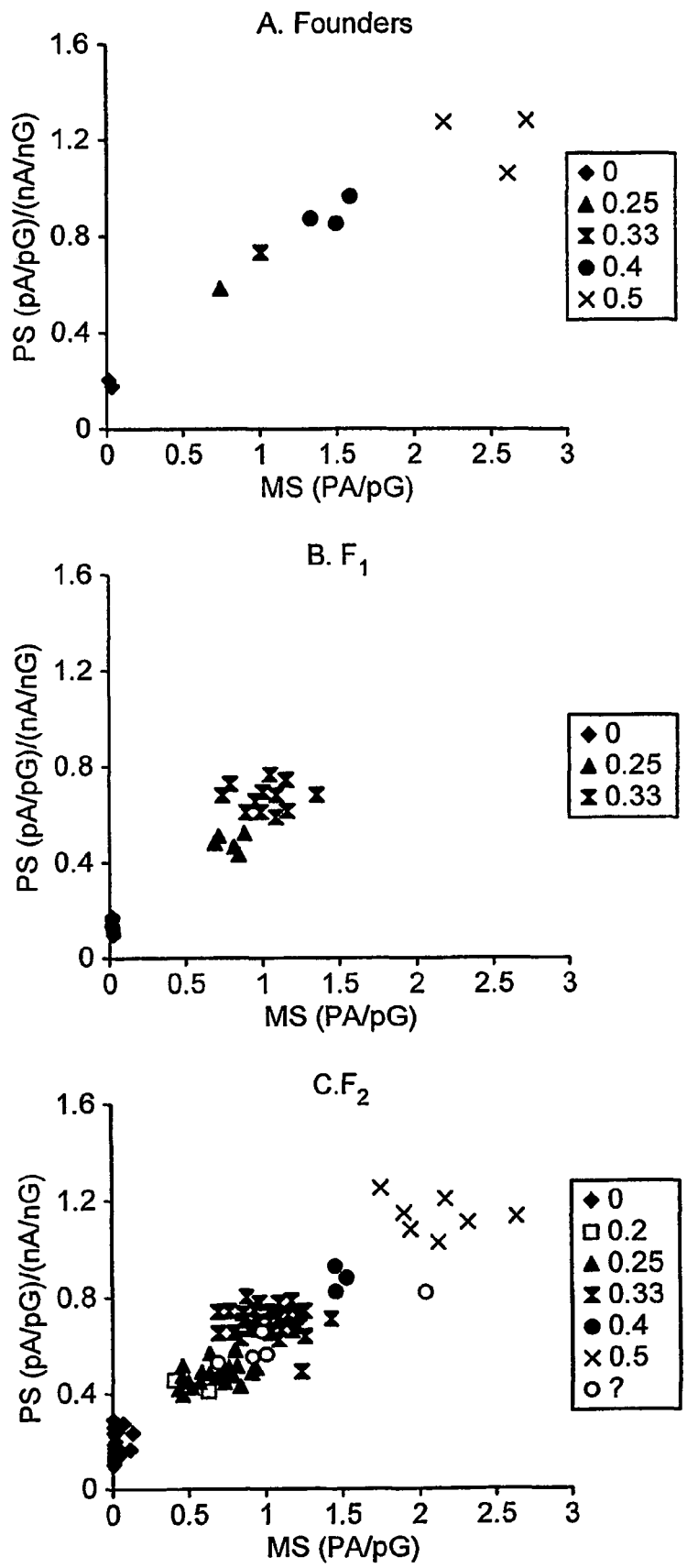

Altschul et al., "Basic Local Alignment Search Tool," J. Mol. Biol. (1990) 215, pp. 403-410, Academic Press, Ltd.

Chowdhary et al., "FISH on metaphase and interphase chromosomes demonstrates the physical order of the genes for GPI, CRC, and LIPE in pigs," Cytogenet Cell Genet 71:175-178 (1995), S. Karger AG, Basel.

Hough et al., "Rump white inversion in the mouse disrupts dipeptidyl aminopeptidase-like protein 6 and causes dysregulation of Kit expression," Proc. Natl. Acad. Sci. USA, vol. 95, pp. 13800-13805, Nov. 1998.

Berrozpe et al., "The $W^{sh}$, $W^{57}$, and Ph Kit Expression Mutations Define Tissue-Specific Control Elements Located Between -23 and—154 kb Upstream of Kit," Blood, vol. 94, No. 8 Oct. 15, 1999: pp. 2658-2666, The American Society of Hematology.

Marklund et al., "Close association between sequence polymorphism in the KIT gene and the roan coat color in horses," Mammalian Genome 10, 283-288 (1999), Springer-Verlag New York Inc.

Reinsch et al., "A QTL for the Degree of Spotting in Cattle Shows Synteny with the KIT Locus on Chromosome 6," The Journal of Heredity, 1999, 90:629-634, The American Genetic Association.

Marklund et al., "Molecular Basis for the Dominant White Phenotype in the Domestic Pig," Genome Research 8:826-833, 1998, Cold Spring Harbor Laboratory Press.

Giuffra et al., "The Belt mutation in pigs is an allele at the Dominant white (I/KIT) locus," Mammalian Genome 10, 1132-1136 (1999), Springer-Verlag New York Inc.

Moller et al., "Pigs with the dominant white coat color phenotype carry a duplication of the KIT gene encoding the mast/stem cell growth factor receptor," Mammaliam Genome 7, 822-830 (1996), Springer-Verlag New York Inc.

Alderborn et al., "Determination of Single-Nucleotide Polymorphisms by Real-time Pyrophosphate DNA Sequencing," Genome Research, 10: 1249-1258, 2000, Cold Spring Harbor Laboratory Press.

* cited by examiner

```
                    10         20         30         40         50         60
BAC953F11   ATCTGAGAAGGCTACATACTGTATGATTCCAAGGGTCATGGCTTGAAAAAGAGACTGACC
BAC1041B3   ------------------------------C-A-ATGACA--CTGG--AT-G-AA-A-
BAC832E11   CAGAT-AC-TAAAG--G-TCAGTG-T-G--------------------------------
```

FIG. 9 BAC clone 1041B3

```
TCTAAGAACCAAATACATGGAGAGAGAGTTCTTGTCCATGGATAGGAAAA
GACTATATTGTCAAGATGTCAGTTCTTTCCAGCTTGATCTAAAGATTCAG
TGCAATTCCAATAAAAACCTCAGAAGGTTATTTAATAGATATTGATAGAC
NAACTGATTCTAATGTTTATGTGGAGAAGCAGGAGACCTAGAATAGCCAA
CACGATATTGAAGGAGAAGACCAAATTTGGAGGACTTATGCTACTCAACT
TTAAGACTTACTATAAAGCAACAGTAATCAAGATAGCATGGTATTGACAA
AAGAAGAGACAAATAGAACAGAATAGAGAGCTAAAAATAGCTTTCCATAG
ATATAGTCAACTTGATTTTTGACAAAGGAGCAAAAGCAACATAATGGTGC
AAAGATAGTCTCTTCAACAACTGGTGTGGGAACAACTGGACATTCATGTG
TTAAAAAAAAACAGCTAGACAACAGACATTACAACCTTCACACAAATCAA
CCCTAGCTGATCACAGACCTAAGTGTAGAATGCAAAATTATAAAATTCCT
AGATGATAACACAGGTAGGAGAAAATCTAGATGATCCTGGGTATGGCAAT
GCCTTTTTACATGTACCATCAAAGGCAAAATTCATGAAAAATTAATAAGC
TGGACCTAATTAAAATTAAAAGCTTCTCTGTAAAAGATAATGAGCATGAG
AAGACAATCCACAGACTTGGAGAAAATATTTGCAAAAGACATATCTGATA
AAAGACTCTCATCAAAATGTACAAAGAACACTTAAAATTCAATAACAAGA
AAATAAACACGATTAAAAAATGGGCAGAGACCCTAACAGATACCTCACC
AAAGATATACAGATGGCAATATGCATATGAAAAGATGCTCCATACCATAT
GTCAACAGGGAGATACAAATGAAAACATCAGTGAGATGCTATCACATCTC
TTAGAATGACCAAAATCTGGAACACTGATAACATGAAATACTGGCAAGAG
TGTAGAGTAATAGGAAATCATATACATTTCTGATAGGAATTCAAAATACT
ACAGTCATCTTGGAAGACAGTTTGCCAGTTTCTTACAAAACTAAACTAAA
GATACTCTTACCGTTCAATCCAGCAATCACAACCTTTGGTATTTACTCAA
AGGAGGTGAGAACTTATGTCCTATAAAACCTGCACACAGATGTTTATGAT
AACTTTACTCATCATTTCCAAAACTTGCAAGAAACCAAGATGTCCTTCAG
TGAGTGAATGGACAGATCAACTATGCTACATCCAGGCAATTGAATATTAT
TTAATACTAAAAAGAAATCAGCTACCAAGCCATGAAATTACGTGGAAGAA
CCTTAAATATGCATTACTAAGTGAAAGAAGTCAATCTGAGAAGGCTACAT
ACTGTATGATTCCAACGATATGACATTCTGGAAATGGCAAAACCATGGAG
ACAGCGAAAGATCAGTAGTTTCCAGGGATAAACAGGCAAAGCCGACATG
ATTTTTAGGGAGTTTAAATACTCTGTATGACACTATAATGATGGATCTAT
GTCATTATACATTTGTCCAAACCCACAGAATGTACAACACCAAGAATGAA
CCATAAAGTAAACTCTAGACTTTGGGTGATTATGATGTGCCAGTGTAGAT
GCATCCTTGACCACCAATGTGTCATTTCAGTGATGTTGGTAATGGGGGAG
GCTATGCATGTGTGGGCAGAGGGCATATGAGAAATCTCTGTACCTTCCTC
TCAACAGTGACATGACCCTAAAACTGCTCTTAAAAAATAGTCTTTAAAAA
ACTTCAACATGTTTCCAAATAGTCTTGGGTCAAAGAATGAATCAGAAGAA
AAATTATGAATAATTTTAACTAAATGGTAATGAAAATATAATATTTCAAA
ATATATGGATTATGACTAAAGTAGTGCTTAGGAAAATTTTCATAGCTTAA
AATACATTAGAGAATAAGGAAAGAATAAAATAAGTGAGTTAATGTTTCAC
CTTAAGAAGCTAAAGAAAAGAAAAATAAGAAAAAAAGGAATAATAAAGAC
AAGTGTAAAATCCATAAAACAGAAAATAGATAAATAATAGAGAATGTCAA
CAAAGACAAAAGTTGGTCCTTAAGAGGATTAAAAAATTTCAAAAAACCCT
TAGCAAAACTTGACAACAACAACAATAAAAAAGAAAACACAGATTACCTA
TACCTGACTTGAAAGAGGACATGTTACTCAAATCACAGAGATATTAAGAA
AATAGGGAGATAACATGAATTGATTTAAACTAATAAATTTGAAAATTTAG
ATGAAATAGACAAATTCCTTGAAAAACACAACTTACCAAAACCAACACAA
GAAGAAATAGAATATCTAAATAACCCTATGTATTTTAGAGAAATTGAATT
TGTAATTAAAATCTTTCCCACAAATTTTTTTGTGTGTCTGTCTTTTTTTC
GGTCTTTTTAGGGCCTCACCCGCGCCATATGGAGGTTCCCAGTCTTGGGG
TCCAATCGGAGCTGTAGCCGCTAACCTACTTCAGAGCCACAGCAACAGAG
GATCCGAGCCACAGCTTACAGCAACACTGGGTCCTTAACCCACTGAGTGA
GGCCAGGGATGGAACCTGCATCCTTATGGATGCTAGTTGGTTTGCTAACT
G
```

FIG. 10 BAC clone 832

```
CCCCGCCAATGAATCTCATTCATTATCTACCATTGTATACAAAAGTTAAC
TCAAAATGGTTTGGTAGGTCTACTGTAAAACATAAAATTCTGGAAGAACG
TATGAGAAAGGCTTGACTGATTTCACGTTCTTTAAACAGATTACTCTTAA
AGACACAATTAATAAAATGAATATATTTGCAAAAGATGTTTTGGTAGAAT
ATATTTGCAAAAACATATCTGCTAAAAGGTTTATATTCAGAATATATTAA
AAAAATGATTTCAACTCAACAAAGAGAAGATAACCTAACAAGTAAAAAAA
AAAATAGCAAGAGATTTGAACAGATATTTCATCAAAAAAAAAATGTGGAT
GGCAAACAAATACATAAAAAGATGCTCAAAATCATTAACCATTAGAAAAA
TACAACTAAAATCCAAATGGTATACCACAATATACCTACCAGAATTACTA
AAATTACAAAGACTGACAATACCAACTATTGGCAAGGGTGTAGAGCAATT
GTGATTCTCATTTATTGTTGCTGGGGTTACAAAATAATATAGCCACGTTG
AAAAAGAGATTGACAACTTCCTAAAAATGAGGTAATTACCATATGACCTA
CCAATTCCATTCCTATGTGTTTGCCCAAGAGAAATGAAAACATACACCCA
CACAAAGATTCATGTGAAATGTTCTTTTCAGCATTATTAATAAGATCCCC
AAACTGGAAATAATCCAGTGTCCATCAACACATAAATGAATAAACAAATT
GTGGCATAACTGTACAATGGAATAGTATTGAGCAATAAAAAGGAATGAAC
AGATAACATAAAGCAGATCAGTGGTTGCCAAGGGTCATGGCTTGAAAAAG
AGACTGACCTCAAAAGAGCCACGAGACAACATTTAAAGTAATAGAAATGT
TCTGTATCTATTTTGGTGATAGTTACATGACTGCCATATTTGTCAAAACT
CATCAAATTGTACATCTAAAATAGATGCCTTTATCATATGTGATTCCATC
TCAAAGCTGCCTTCAAAACTCAAGCCATCTACATCCATATTGTATGCAAG
TAAGAAGGATGCTGTGAACCAGAGAGTAGCAAAATTTTTCTGTAAAGGAC
CTGACGGTGAATGTTTTACTTTTGAATGTATGTCTATAGCCTGTCACAAC
TGCTGGACTCTGTCTTGGTAACATCAAAGCAGGTATAGACAACAGGTTGA
ATGAATAGGTGTGGCTGTGTTTCAATAAAACTTAGTTTTAAACGCTGAAA
TTTACATTTCATCTTTCTCATAAGTCATGAAATATTATTCTTCCTCTGAC
TTTTTCCCCCAAATAATTTACAAATGTGAGACACTCTCTTAGCTAGCAGG
CTATCCAAAAACAGATGATAGACCAGATTTGATCCACAGGTTGTAGTTTG
CCAACTCCTCTAAACAAATGTTAGTAAAAAATACAACAATTATCGTAACT
GTATCATAGAAGTAGGATGCGGGTGAAACATCGATATTCCATTCATGGTT
ACATGTTGGAGATCTGTGTAGACTAGAAATAACAAGCTCCATTTTTCACA
TATTCTTCAATAGTACAATTTTGTTTGCTATGTCATATTACTTTGGAGTA
GTAGGCTTAAAAAAATCAAGGCGTTCCCACTGTGTGCTCCAACGAGGAGC
CATGAAGATGTGGTTGTGAGCCCTGGTCTCACTCAGTGGGTGAAGGATCC
AGTATTGCCGTGAGCTGTAGTGTAGATATATTTATATGTGATTTGCTGAA
TGAATAGTCCGGCTTTACAAAAGAAGACACCTTCATGGGAACATCACCT
AACAACTGCCATAGAAGTGACCCCAAATTAGCGAGAACCATTGTCCTGAG
ACACCCAAGGATGGTGGGAGAAAACACCATTCACACCAGCTGGCGGGCCC
AGCCAGTCAGGAAAGAGGACTGATCCCACTCAGGGGGTGGGTATCACAG
ACCCCGAGAACCCCTAAGGGGAAGATCTTCCCTTTGGCAAATACATCCTA
CAAGGTTTTGAGCAATTGTCAAAATGGAGAACTTTTAGTAACCATGCCTT
CCATTGAAAAAGTCATGGCCATTTGTCTTCTTTTCCTTCACTTAACTCCT
TTCGAATATTTTCTTGTTGAAATGCTTGTAAATAGAAAGGGCAGATTCTT
TAGTGGGAGGGTATTTCCCAGGTTCCGGAGAAGTTGTCTGAGGGAAGAAG
AGTGTGCTTGATTCCCAGAAGGCAAGTCAAGGCTTCTGAGTTACAGATGC
CCAAAGCACAAGAACTGTAATACAGCATATTTCTTCATAAAGCCCATTCT
GCTGTCTCAGGGCTGCAGTGTCAAATCGTAGAAACCTATGTCTTTGAAGT
TCTTGACATATAATGTTGACATTTTCAGCCTCTCAAGTGTATGATGAAAG
ATTAGAATGATGGTGGTGAACAAGAATGACCTATAGAAAGACATTTTCTG
AAGCGGTAAAAAAAACGTTTTTTTTTTTTAATGGATGGAGAATTTTTCT
```

```
TTTGAACTGTGAGTTGNCCATGAAGGGAAAAAAAAAAATGGAAAGAAAAG
AAAGAAAACAGATCAAAGCAACATAAAAATTGGTTTTAATTTTCTTTACA
AAATCTTGTGGGAACAAACAAATACAACATCTTTTTTGTTTTGTTTTGTT
TTGTTTTGGGGGGGGGGGCATGCCCATAGCATGCAAAAGTTCCTGGGCCA
GGGAATGAACTATGCCACTGCAGTGAAAACTGCTGGATCTTTAACCACTA
GGCCACCAGAGAATCTCAACAAATACAAACTTTGAGCAAATTTGTGTTTG
AAACATATTCCTTTCTTGCCACGTAGTAGAAAGTATTTTCATGTGAAAAA
TAGTGTCTATATTTTCCTAGTACTTAAGAATTTTGTCCAGGGAATGCCCG
TAGTGACTCATCAGTAACGAACCCTACTAGTATCCATGAGGATGTGGGTT
CAATCCCTGGCCTCACTCAGTAGGTTAAGGATCCCGGCTTTGCTGTGGCT
GTGGTGTAGGCTGGCAGCTGTAGCTCTGATTCGACCCCTGCCCTGAGAAC
TTCCATATGCCACAGGTGTGGCTCTACAGAAAAGAAAAAGAATTGTGT
CCAAATGATTCTGGTGTTGTCACATAAAGATCAGAGCTGGACCAAGTTTG
AATTCAAAGGTTGTTGTCTAAATATTTGTTGGGATAAACTGGGAATCGGA
ATTAACATATACATACTACTACATAAAAACAGCTAAGCAAAAAAAGAA
CCTACTATAGAGCACAGGGGACTTTATTTAGTACTTCCAAATAACCTATA
GTGGACAATAATATGAAAAATACATATATACCTGAATCACCTTGCTGTA
CACAGTAATACAACATTGCAAATCAACTATACTTCAATTTAAAAGGAAAT
AAAAATAAAATATTTTAAAAATTCTTGTTCTTACTCTTGGGCTTGAAAGA
GAACATTAATGAGGAGTTCCCATTGTGGTACAGCGGAAAAGAATCTGACT
AGGAACCATGAGGTTGCAGGTTCGATCCCTGGCCTCGCTCAGTAGGTTAA
GGATCCGGCATCGCCATGAGCTGTGCTGGGAGTCTCAGATGTGGCTTGGA
TCCTGTGTTGCTGTGGCTGTGGTGTTGGCCACCAGCTGTAGATCTGATTC
AACCCCTAGCCTGGGAACCTCCATATGCCACAGGTGCAGCCCTAAAAAGC
AAAAAAAANNNNNNNNNNNNNNNNNNNNGAGAGAGAGAGAGAGAGAGG
GAGAACATTAATGAGTTCCCTCGCTCTCCCTGACTCTCTC
```

FIG. 10 CONT'D

FIG. 11 BAC clone 953

```
TCTAAGAACCAAATACATGGAGAGAGAGTTCTTGTCCATGGATAGGAAAA
GACTATATTGTCAAGATGTCAGTTCTTTCCAGCTTGATCTAAAGATTCAG
TGCAATTCCAATAAAAACCTCAGAAGGTTATTTAATAGATATTGATAGAC
AAACTGATTCTAATGTTTATGTGGAGAAGCAGGAGACCTAGAATAGCCAA
CACGATATTGAAGGAGAAGACCAAATTTGGAGGACTTATGCTACTCAACT
TTAAGACTTACTATAAAGCAACAGTAATCAAGATAGCATGGTATTGACAA
AAGAAGAGACAAATAGAACAGAATAGAGAGCTAAAAATAGCTTTCCATAG
ATATAGTCAACTTGATTTTTGACAAAGGAGCAAAAGCAACATAATGGTGC
AAAGATAGTCTCTTCAACAACTGGTGTGGGAACAACTGGACATTCATGTG
TTAAAAAAAAACAGCTAGACAACAGACATTACAACCTTCACACAAATCAA
CCCTAGCTGATCACAGACCTAAGTGTAGAATGCAAAATTATAAAATTCCT
AGATGATAACACAGGTAGGAGAAAATCTAGATGATCCTGGGTATGGCAAT
GCCTTTTTACATGTACCATCAAAGGCAAAATTCATGAAAAATTAATAAGC
TGGACCTAATTAAAATTAAAAGCTTCTCTGTAAAGATAATGAGCATGAG
AAGACAATCCACAGACTTGGAGAAAATATTTGCAAAAGACATATCTGATA
AAAGACTCTCATCAAAATGTACAAAGAACACTTAAAATTCAATAACAAGA
AAATAAACACGATTAAAAAATGGGCCAGAGACCCTAACAGATACCTCACC
AAAGATATACAGATGGCAATATGCATATGAAAAGATGCTCCATACCATAT
GTCAACAGGGAGATACAAATGAAAACATCAGTGAGATGCTATCACATCTC
TTAGAATGACCAAAATCTGGAACACTGATAACATGAAATACTGGCAAGAG
TGTAGAGTAATAGGAAATCATATACATTTCTGATAGGAATTCAAAATACT
ACAGTCATCTTGGAAGACAGTTTGCCAGTTTCTTACAAAACTAAACTAAA
GATACTCTTACCGTTCAATCCAGCAATCACAACCTTTGGTATTTACTCAA
AGGAGGTGAGAACTTATGTCCTATAAAACCTGCACACAGATGTTTATGAT
AACTTTACTCATCATTTCCAAAACTTGCAAGAAACCAAGATGTCCTTCAG
TGAGTGAATGGACAGATCAACTATGCTACATCCAGGCAATTGAATATTAT
TTAATACTAAAAGAAATCAGCTACCAAGCCATGAAATTACGTGGAAGAA
CCTTAAATATGCATTACTAAGTGAAAGAAGTCAATCTGAGAAGGCTACAT
ACTGTATGATTCCAAGGGTCATGGCTTGAAAAAGAGACTGACCTCAAAAG
AGCCACGAGACAACATTTAAAGTAATAGAAATGTTCTGTATCTATTTTGG
TGATAGTTACATGACTGCCATATTTGTCAAAACTCATCAAATTGTACATC
TAAAATAGATGCCTTTATCATATGTGATTCCATCTCAAAGCTGCCTTCAA
AACTCAAGCCATCTACATCCATATTGTATGCAAGTAAGAAGGATGCTGTG
AACCAGAGAGTAGCAAAATTTTTCTGTAAAGGACCTGACGGTGAATGTTT
TACTTTTGAATGTATGTCTATAGCCTGTCACAACTGCTGGACTCTGTCTT
GGTAACATCAAAGCAGGTATAGACAACAGGTTGAATGAATAGGTGTGGCT
GTGTTTCAATAAAACTTAGTTTTAAACGCTGAAATTTACATTTCATCTTT
CTCATAAGTCATGAAATATTATTCTTCCTCTGACTTTTTCCCCCAAATAA
TTTACAAATGTGAGACACTCTCTTAGCTAGCAGGCTATCCAAAAACAGAT
GATAGACCAGATTTGATCCACAGGTTGTAGTTTGCCAACTCCTCTAAACA
AATGTTAGTAAAAATACAACAATTATCGTAACTGTATCATAGAAGTAGG
ATGCGGGTGAAACATCGATATTCCATTCATGGTTACATGTTGGAGATCTG
TGTAGACTAGAAATAACAAGCTCCATTTTTCACATATTCTTCAATAGTAC
AATTTGTTTGCTATGTCATATTACTTTGGAGTAGTAGGCTTAAAAAAAT
CAAGGCGTTCCCACTGTGTGCTCCAACGAGGAGCCATGAAGATGTGGTTG
TGAGCCCTGGTCTCACTCAGTGGGTGAAGGATCCAGTATTGCCGTGAGCT
GTAGTGTAGATATATTTATATGTGATTTGCTGAATGAATAGTCCGGGCTT
TACAAAGAAGACACCTTCATGGGAACATCACCTAACAACTGCCATAGAA
GTGACCCCAAATTAGCGAGAACCATTGTCCTGAGACACCCAAGGATGGTG
GGAGAAAACACCATTCACACCAGCTGGCGGGCCCAGCCAGTCAGGAAAGA
```

```
GGACTGATCCCACTCAGGGGGTGGGGTATCACAGACCCCGAGAACCCCTA
AGGGGAAGATCTTCCCTTTGGCAAATACATCCTACAAGGTTTTGAGCAAT
TGTCAAAATGGAGAACTTTTAGTAACCATGCCTTCCATTGAAAAAGTCAT
GGCCATTTGTCTTCTTTTCCTTCACTTAACTCCTTTCGAATATTTTCTTG
TTGAAATGCTTGTAAATAGAAAGGGCAGATTCTTTAGTGGGAGGGTATTT
CCCAGGTTCCGGAGAAGTTGTCTGAGGGAAGAAGAGTGTGCTTGATTCCC
AGAAGGCAAGTCAAGGCTTCTGAGTTACAGATGCCCAAAGCACAAGAACT
GTAATACAGCATATTTCTTCATAAAGCCCATTCTGCTGTCTCAGGGCTGC
AGTGTCAAATCGTAGAAACCTATGTCTTTGAAGTTCTTGACATATAATGT
TGACATTTTCAGCCTCTCAAGTGTATGATGAAAGATTAGAATGATGGTGG
TGAACAAGAATGACCTATAGAAAGACATTTTCTGAAGCGGTAAAAAAAAC
GTTTTTTTTTTTTAATGGATGGAGAATTTTTCTTTTGAACTGTGAGTTG
ACCATGAAGGGAAAAAAAAAATGGAAAGAAAAGAAAGAAAACAGATCAAA
GCAACATAAAAATTGGTTTTAATTTTCTTTACAAAATCTTGTGGGAACAA
ACAAATACAACATCTTTTTTGTTTTGTTTTGTTTTGTTTTGGGGGGGGGG
GCATGCCCATAGCATGCAAAAGTTCCTGGGCCAGGGAATGAACTATGCCA
CTGCAGTGAAAACTGCTGGATCTTTAACCACTAGGCCACCAGAGAATCTC
AACAAATACAAACTTTGAGCAAATTTGTGTTTGAAACATATTCCTTTCTT
GCCACGTAGTAGAAAGTATTTTCATGTGAAAAATAGTGTCTATATTTTCC
TAGTACTTAAGAATTTTGTCCAGGGAATGCCCGTAGTGACTCATCAGTAA
CGAACCCTACTAGTATCCATGAGGATGTGGGTTCAATCCCTGGCCTCACT
CAGTAGGTTAAGGATCCCGGCTTTGCTGTGGCTGTGGTGTAGGCTGGCAG
CTGTAGCTCTGATTCGACCCCTGCCCTGAGAACTTCCATATGCCACAGGT
GTGGCTCTACAGAAAAGAAAAAGAATTGTGTCCAAATGATTCTGGTGT
TGTCACATAAGATCAGAGCTGGACCAAGTTTGAATTCAAAGGTTGTTGT
CTAAATATTTGTTGGGATAAACTGGGAATCGGAATTAACATATACATACT
ACTACATAAAAAACAGCTAAGCAAAAAAAAGAACCTACTATAGAGCACAG
GGGACTTTATTTAGTACTTCCAAATAACCTATAGTGGACAATAATATGAA
AAAATACATATATACCTGAATCACCTTGCTGTACACAGTAATACAACATT
GCAAATCAACTATACTTCAATTTAAAAGGAAATAAAAATAAAATATTTTA
AAAATTCTTGTTCTTACTCTTGGGCTTGAAAGAGAACATTAATGAGGAGT
TCCCATTGTGGTACAGTGGAAAAGAATCTGACTAGGAACCATGAGGTTGC
AGGTTCGATCCCTGGCCTCGCTCAGTAGGTTAAGGATCCGGCATCGCCAT
GAGCTGTGCTGGGAGTCTCAGATGTGGCTTGGATCCTGTGTTGCTGTGGC
TGTGGTGTTGGCCACCAGCTGTAGATCTGATTCAACCCCTAGCCTGGAA
CCTCCATATGCCACAGGTGCAGCCCTAAAAAGCAAAAAAAANNNNNNNNN
NNNNNNNNNGAGAGAGAGAGAGAGAGAGAGGGAGAACATTAATGAGTT
CCCTCGCTCTCCCTGACTCTCTCTCTCTCATTCCCTGTCTTTGCTATG
TATGATATTTACTTGAATCTAAAACATATATTTTTTGCATCTTAATGTG
TCTGAATTCAGAATATCTTATAATGCATGGTGTCTCTCAATTACACTCAT
CAGCAATTTTTCTTTCTTTGTGGTACATAAAATAATATTGAATCTCATAG
TTGATATTGTCTAAGAGTCCATGAAATTAGATATACATGA
```

FIG. 11 CONT'D

SEQUENCE LISTING

<160> NUMBER OF SEQ ID NOS: 23

<210> SEQ ID NO 1
<211> LENGTH: 22
<212> TYPE: DNA
<213> ORGANISM: Artificial

```
<220> FEATURE:
<223> OTHER INFORMATION: Oligonucleotide Primer

<400> SEQUENCE: 1
gtattcacag agacttggcg gc                                          22

<210> SEQ ID NO 2
<211> LENGTH: 26
<212> TYPE: DNA
<213> ORGANISM: Artificial
<220> FEATURE:
<223> OTHER INFORMATION: Oligonucleotide Primer

<400> SEQUENCE: 2
aaacctgcaa ggaaaatcct tcacgg                                      26

<210> SEQ ID NO 3
<211> LENGTH: 24
<212> TYPE: DNA
<213> ORGANISM: Artificial
<220> FEATURE:
<223> OTHER INFORMATION: Oligonucleotide Primer

<400> SEQUENCE: 3
ctacctttgc cataccatgc attt                                        24

<210> SEQ ID NO 4
<211> LENGTH: 25
<212> TYPE: DNA
<213> ORGANISM: Artificial
<220> FEATURE:
<223> OTHER INFORMATION: Oligonucleotide Primer

<400> SEQUENCE: 4
ttgcatgccc tctaattaca caatt                                       25

<210> SEQ ID NO 5
<211> LENGTH: 24
<212> TYPE: DNA
<213> ORGANISM: Artificial
<220> FEATURE:
<223> OTHER INFORMATION: Oligonucleotide Primer

<400> SEQUENCE: 5
ccacaatata cctaccagaa ttac                                        24

<210> SEQ ID NO 6
<211> LENGTH: 22
<212> TYPE: DNA
<213> ORGANISM: Artificial
<220> FEATURE:
<223> OTHER INFORMATION: Oligonucleotide Primer

<400> SEQUENCE: 6
aacctgtgga tcaaatctgg tc                                          22

<210> SEQ ID NO 7
<211> LENGTH: 22
<212> TYPE: DNA
<213> ORGANISM: Artificial
<220> FEATURE:
<223> OTHER INFORMATION: Oligonucleotide Primer

<400> SEQUENCE: 7
gttcaatcca gcaatcacaa cc                                          22
```

<210> SEQ ID NO 8
<211> LENGTH: 22
<212> TYPE: DNA
<213> ORGANISM: Artificial
<220> FEATURE:
<223> OTHER INFORMATION: Oligonucleotide Primer

<400> SEQUENCE: 8
aacctgtgga tcaaatctgg tc                                    22

<210> SEQ ID NO 9
<211> LENGTH: 22
<212> TYPE: DNA
<213> ORGANISM: Artificial
<220> FEATURE:
<223> OTHER INFORMATION: Oligonucleotide Primer

<400> SEQUENCE: 9
gttcaatcca gcaatcacaa cc                                    22

<210> SEQ ID NO 10
<211> LENGTH: 23
<212> TYPE: DNA
<213> ORGANISM: Artificial
<220> FEATURE:
<223> OTHER INFORMATION: Oligonucleotide Primer

<400> SEQUENCE: 10
ttttaatcct cttaaggacc aac                                   23

<210> SEQ ID NO 11
<211> LENGTH: 23
<212> TYPE: DNA
<213> ORGANISM: Artificial
<220> FEATURE:
<223> OTHER INFORMATION: Oligonucleotide Primer

<400> SEQUENCE: 11
taagtgaaag aagtcaatct gag                                   23

<210> SEQ ID NO 12
<211> LENGTH: 21
<212> TYPE: DNA
<213> ORGANISM: Artificial
<220> FEATURE:
<223> OTHER INFORMATION: Oligonucleotide Primer

<400> SEQUENCE: 12
ggcagtcatg taactatcac c                                     21

<210> SEQ ID NO 13
<211> LENGTH: 20
<212> TYPE: DNA
<213> ORGANISM: Artificial
<220> FEATURE:
<223> OTHER INFORMATION: Oligonucleotide Primer

<400> SEQUENCE: 13
gcagctgcca acctattcca                                       20

<210> SEQ ID NO 14
<211> LENGTH: 21
<212> TYPE: DNA
<213> ORGANISM: Artificial
<220> FEATURE:
<223> OTHER INFORMATION: Oligonucleotide Primer -continued

```
<400> SEQUENCE: 14
tgggtttagg atgcagcatt g                                              21

<210> SEQ ID NO 15
<211> LENGTH: 27
<212> TYPE: DNA
<213> ORGANISM: Artificial
<220> FEATURE:
<223> OTHER INFORMATION: Oligonucleotide Primer

<400> SEQUENCE: 15
tgcaaaagca cacttcatct gacggct                                        27

<210> SEQ ID NO 16
<211> LENGTH: 27
<212> TYPE: DNA
<213> ORGANISM: Artificial
<220> FEATURE:
<223> OTHER INFORMATION: Oligonucleotide Primer

<400> SEQUENCE: 16
catctgcacc ctacaccaca gctcaca                                        27

<210> SEQ ID NO 17
<211> LENGTH: 22
<212> TYPE: DNA
<213> ORGANISM: Artificial
<220> FEATURE:
<223> OTHER INFORMATION: Oligonucleotide Primer
<220> FEATURE:
<221> NAME/KEY: misc_feature
<222> LOCATION: (8)..(8)
<223> OTHER INFORMATION: n is Inosine

<400> SEQUENCE: 17
taattacntg gtcaaaggaa ac                                             22

<210> SEQ ID NO 18
<211> LENGTH: 60
<212> TYPE: DNA
<213> ORGANISM: Sus scrofa

<400> SEQUENCE: 18
atctgagaag gctacatact gtatgattcc aagggtcatg gcttgaaaaa gagactgacc    60

<210> SEQ ID NO 19
<211> LENGTH: 60
<212> TYPE: DNA
<213> ORGANISM: Sus scrofa

<400> SEQUENCE: 19
atctgagaag gctacatact gtatgattcc aacgatatga cattctggaa atggcaaaac    60

<210> SEQ ID NO 20
<211> LENGTH: 60
<212> TYPE: DNA
<213> ORGANISM: Sus scrofa

<400> SEQUENCE: 20
cagataacat aaagcagatc agtggttgcc aagggtcatg gcttgaaaaa gagactgacc    60

<210> SEQ ID NO 21
<211> LENGTH: 2650
<212> TYPE: DNA
<213> ORGANISM: Sus scrofa
```

```
<220> FEATURE:
<221> NAME/KEY: misc_feature
<222> LOCATION: (151)..(151)
<223> OTHER INFORMATION: n is a, c, g, or t

<400> SEQUENCE: 21
tctaagaacc aaatacatgg agagagagtt cttgtccatg gataggaaaa gactatattg      60
tcaagatgtc agttctttcc agcttgatct aaagattcag tgcaattcca ataaaaacct     120
cagaaggtta tttaatagat attgatagac naactgattc taatgtttat gtggagaagc     180
aggagaccta gaatagccaa cacgatattg aaggagaaga ccaaatttgg aggacttatg     240
ctactcaact ttaagactta ctataaagca acagtaatga agatagcatg gtattgacaa     300
aagaagagac aaatagaaca gaatagagag ctaaaaatag cttcccatag atatagtcaa     360
cttgattttt gacaaaggag caaaagcaac ataatggtgc aaagatagtc tcttcaacaa     420
ctggtgtggg aacaactgga cattcatgtg ttaaaaaaaa acagctagac aacagacatt     480
acaaccttca cacaaatcaa ccctagctga tcacagacct aagtgtagaa tgcaaaatta     540
taaaattcct agatgataac acaggtagga gaaaatctag atgatcctgg gtatggcaat     600 gccttttttac atgtaccatc aaaggcaaaa ttcatgaaaa attaataagc tggacctaat     660
taaaattaaa agcttctctg taaaagataa tgagcatgag aagacaatcc acagacttgg     720
agaaaatatt tgcaaaagac atatctgata aaagactctc atcaaaatgt acaaagaaca     780
cttaaaattc aataacaaga aaataaacac gattaaaaaa tgggccagag accctaacag     840
atacctcacc aaagatatac agatggcaat atgcatatga aaagatgctc ataccatat     900 gtcaacaggg agatacaaat gaaaacatca gtgagatgct atcacatctc ttagaatgac     960
caaaatctgg aacactgata acatgaaata ctggcaagag tgtagagtaa taggaaatca    1020
tatacatttc tgataggaat tcaaaatact acagtcatct tggaagacag tttgccagtt    1080
tcttacaaaa ctaaactaaa gatactctta ccgttcaatc cagcaatcac aacctttggt    1140
atttactcaa aggaggtgag aacttatgtc ctataaaacc tgcacacaga tgtttatgat    1200
aactttactc atcatttcca aaacttgcaa gaaaccaaga tgtccttcag tgagtgaatg    1260
gacagatcaa ctatgctaca tccaggcaat tgaatattat ttaatactaa aaagaaatca    1320
gctaccaagc catgaaatta cgtggaagaa ccttaaatat gcattactaa gtgaaagaag    1380
tcaatctgag aaggctacat actgtatgat tccaacgata tgacattctg gaaatggcaa    1440
aaccatggag acagcgaaaa gatcagtagt ttccagggat aaacaggcaa agccgacatg    1500
atttttaggg agtttaaata ctctgtatga cactataatg atggatctat gtcattatac    1560
atttgtccaa acccacagaa tgtacaacac caagaatgaa ccataaagta aactctagac    1620
tttgggtgat tatgatgtgc cagtgtagat gcatccttga ccaccaatgt gtcatttcag    1680
tgatgttggt aatgggggag gctatgcatg tgtgggcaga gggcatatga gaaatctctg    1740
taccttcctc tcaacagtga catgacccta aaactgctct taaaaaatag tcttaaaaa     1800 acttcaacat gtttccaaat agccttgggt caaagaatga atcagaagaa aaattatgaa    1860
taattttaac taaatggtaa tgaaaatata atatttcaaa atatatgcat tatgactaaa    1920
gtagtgctta ggaaaatttt catagcttaa aatacattag agaataagga aagaataaaa    1980
taagtgagtt aatgtttcac cttaagaagc taaagaaaag aaaataaga aaaaaggaa      2040 taataaagac aagtgtaaaa tccataaaac agaaaataga taaataatag agaatgtcaa    2100
caaagacaaa agttggtcct taagaggatt aaaaaatttc aaaaaaccct tagcaaaact    2160
```

```
tgacaacaac aacaataaaa aagaaaacac agattaccta tacctgactt gaaagaggac    2220
atgttactca aatcacaaga tattaagaaa atagggagat aacatgaatt gatttaaact    2280
aataaatttg aaaatttaga tgaaatagac aaattccttg aaaaacacaa cttaccaaaa    2340
ccaacacaag aagaaataga atatctaaat aaccctatgt attttagaga aattgaattt    2400
gtaattaaaa tctttcccac aaattttttt gtgtgtctgt ctttttttcg gtctttttag    2460
ggcctcaccc gcgccatatg gaggttccca gtcttgggt ccaatcggag ctgtagccgc     2520
taacctactt cagagccaca gcaacagagg atccgagcca cagcttacag caacactggg    2580
tccttaaccc actgagtgag gccagggatg gaacctgcat ccttatggat gctagttggt    2640
ttgctaactg                                                            2650
```

<210> SEQ ID NO 22
<211> LENGTH: 3789
<212> TYPE: DNA
<213> ORGANISM: Sus scrofa
<220> FEATURE:
<221> NAME/KEY: misc_feature
<222> LOCATION: (2517)..(2517)
<223> OTHER INFORMATION: n is a, c, g, or t
<220> FEATURE:
<221> NAME/KEY: misc_feature
<222> LOCATION: (3708)..(3725)
<223> OTHER INFORMATION: n is a, c, g, or t

<400> SEQUENCE: 22

```
ccccgccaat gaatctcatt cattatctac cattgtatac aaaagttaac tcaaaatggt      60
ttggtaggtc tactgtaaaa cataaaattc tggaagaacg tatgagaaag gcttgactga     120
tttcacgttc tttaaacaga ttactcttaa agacacaatt aataaaatga atatatttgc     180
aaaagatgtt ttggtagaat atatttgcaa aaacatatct gctaaaaggt ttatattcag     240
aatatattaa aaaatgatt tcaactcaac aaagagaaga taacctaaca agtaaaaaaa      300
aaaatagcaa gagatttgaa cagatatttc atcaaaaaaa aaatgtggat ggcaaacaaa     360
tacataaaaa gatgctcaaa atcattaacc attagaaaaa tacaactaaa atccaaatgg     420
tataccacaa tatacctacc agaattacta aaattacaaa gactgacaat accaactatt     480
ggcaagggtg tagagcaatt gtgattctca tttattgttg ctggggttac aaaataatat     540
agccacgttg aaaagagat tgacaacttc ctaaaaatga ggtaattacc atatgaccta     600
ccaattccat tcctatgtgt ttgcccaaga gaaatgaaaa catacaccca cacaaagatt     660
catgtgaaat gttcttttca gcattattaa taagatcccc aaactggaaa taatccagtg     720
tccatcaaca cataaatgaa taaacaaatt gtggcataac tgtacaatgg aatagtattg     780
agcaataaaa aggaatgaac agataacata agcagatca gtggttgcca agggtcatgg     840
cttgaaaaag agactgacct caaaagagcc acgagacaac atttaaagta atagaaatgt     900
tctgtatcta ttttggtgat agttacatga ctgccatatt tgtcaaaact catcaaattg     960
tacatctaaa atagatgcct ttatcatatg tgattccatc tcaaagctgc cttcaaaact    1020
caagccatct acatccatat tgtatgcaag taagaaggat gctgtgaacc agagagtagc    1080
aaaatttttc tgtaaaggac ctgacggtga atgttttact tttgaatgta tgtctatagc    1140
ctgtcacaac tgctggactc tgtccttggta acatcaaagc aggtatagac aacaggttga    1200
atgaataggt gtggctgtgt ttcaataaaa cttagtttta aacgctgaaa tttacatttc    1260
atctttctca taagtcatga aatattattc ttcctctgac ttttttcccc aaataattta    1320
caaatgtgag acactctctt agctagcagg ctatccaaaa acagatgata gaccagattt    1380
```

```
gatccacagg ttgtagtttg ccaactcctc taaacaaatg ttagtaaaaa atacaacaat    1440
tatcgtaact gtatcataga agtaggatgc gggtgaaaca tcgatattcc attcatggtt    1500
acatgttgga gatctgtgta gactagaaat aacaagctcc attttttcaca tattcttcaa   1560 tagtacaatt ttgtttgcta tgtcatatta ctttggagta gtaggcttaa aaaaatcaag    1620
gcgttcccac tgtgtgctcc aacgaggagc catgaagatg tggttgtgag ccctggtctc    1680
actcagtggg tgaaggatcc agtattgccg tgagctgtag tgtagatata tttatatgtg    1740
atttgctgaa tgaatagtcc gggctttaca aagaagaca ccttcatggg aacatcacct     1800
aacaactgcc atagaagtga ccccaaatta gcgagaacca ttgtcctgag acacccaagg    1860
atggtgggag aaaacaccat tcacaccagc tggcgggccc agccagtcag gaaagaggac    1920
tgatcccact caggggtgg ggtatcacag accccgagaa cccctaaggg gaagatcttc      1980
cctttggcaa atacatccta caaggttttg agcaattgtc aaaatggaga acttttagta    2040
accatgcctt ccattgaaaa agtcatggcc atttgtcttc ttttccttca cttaactcct    2100
ttcgaatatt ttcttgttga aatgcttgta aatagaaagg gcagattctt tagtgggagg    2160
gtatttccca ggttccggag aagttgtctg agggaagaag agtgtgcttg attcccagaa    2220
ggcaagtcaa ggcttctgag ttacagatgc ccaaagcaca agaactgtaa tacagcatat    2280
ttcttcataa agcccattct gctgtctcag ggctgcagtg tcaaatcgta gaaacctatg    2340
tctttgaagt tcttgacata taatgttgac attttcagcc tctcaagtgt atgatgaaag    2400
attagaatga tggtggtgaa caagaatgac ctatagaaag acattttctg aagcggtaaa    2460
aaaaacgttt tttttttttt aatggatgga gaattttct tttgaactgt gagttgncca      2520
tgaagggaaa aaaaaaatg gaaagaaaag aaagaaaaca gatcaaagca acataaaaat      2580
tggttttaat tttctttaca aaatcttgtg ggaacaaaca aatacaacat cttttttgtt    2640
ttgttttgtt ttgttttggg ggggggggca tgcccatagc atgcaaaagt tcctgggcca    2700
gggaatgaac tatgccactg cagtgaaaac tgctggatct ttaaccacta ggccaccaga    2760
gaatctcaac aaatacaaac tttgagcaaa tttgtgtttg aaacatattc ctttcttgcc    2820
acgtagtaga aagtattttc atgtgaaaaa tagtgtctat attttcctag tacttaagaa    2880
ttttgtccag ggaatgcccg tagtgactca tcagtaacga accctactag tatccatgag    2940
gatgtgggtt caatccctgg cctcactcag taggttaagg atcccggctt tgctgtggct    3000
gtggtgtagg ctggcagctg tagctctgat tcgaccctgc cctgagaact tccatatgcc    3060
acaggtgtgg ctctacagaa aaagaaaaaa gaattgtgtc caaatgattc tggtgttgtc    3120
acataaagat cagagctgga ccaagtttga attcaaaggt tgttgtctaa atatttgttg    3180
ggataaactg ggaatcggaa ttaacatata catactacta cataaaaaac agctaagcaa    3240
aaaaaagaac ctactataga gcacagggga ctttatttag tacttccaaa taacctatag    3300
tggacaataa tatgaaaaaa tacatatata cctgaatcac cttgctgtac acagtaatac    3360
aacattgcaa atcaactata cttcaattta aaaggaaata aaaataaaat attttaaaaa    3420
ttcttgttct tactcttggg cttgaaagag aacattaatg aggagttccc attgtggtac    3480
agcggaaaag aatctgacta ggaaccatga ggttgcaggt tcgatccctg gcctcgctca    3540
gtaggttaag gatccggcat cgccatgagc tgtgctggga gtctcagatg tggcttggat    3600
cctgtgttgc tgtggctgtg gtgttggcca ccagctgtag atctgattca accctagcc    3660 tgggaacctc catatgccac aggtgcagcc ctaaaaagca aaaaaaannn nnnnnnnnn      3720
```

-continued

```
nnnnngagag agagagagag agagagaggg agaacattaa tgagttccct cgctctccct    3780
gactctctc                                                            3789
```

<210> SEQ ID NO 23
<211> LENGTH: 4629
<212> TYPE: DNA
<213> ORGANISM: Sus scrofa
<220> FEATURE:
<221> NAME/KEY: misc_feature
<222> LOCATION: (4331)..(4348)
<223> OTHER INFORMATION: n is a, c, g, or t

<400> SEQUENCE: 23

```
tctaagaacc aaatacatgg agagagagtt cttgtccatg gataggaaaa gactatattg      60
tcaagatgtc agttctttcc agcttgatct aaagattcag tgcaattcca ataaaaacct     120
cagaaggtta tttaatagat attgatagac aaactgattc taatgtttat gtggagaagc     180
aggagaccta gaatagccaa cacgatattg aaggagaaga ccaaatttgg aggacttatg     240
ctactcaact ttaagactta ctataaagca acagtaatca agatagcatg gtattgacaa     300
ttaagactta ctataaagca acagtaatca agatagcatg gtattgacaa agaagagac     360 aaatagaaca gaatagagag ctaaaaatag ctttccatag atatagtcaa cttgattttt     420
gacaaaggag caaaagcaac ataatggtgc aaagatagtc tcttcaacaa ctggtgtgga     480
acaactggac attcatgtgt taaaaaaaaa cagctagaca acagacatta caaccttcac     540
acaaatcaac ctagctgatc acagacctaa gtgtagaatg caaaattata aaattcctag     600
atgataacac aggtaggaga aaatctagat gatcctgggt atggcaatgc cttttacat      660 gtaccatcaa aggcaaaatt catgaaaaat taataagctg gacctaatta aaattaaaag     720
cttctctgta aaagataatg agcatgagaa gacaatccac agacttggag aaaatatttg     780
caaaagacat atctgataaa agactctcat caaaatgtac aaagaacact taaaattcaa     840
taacaagaaa ataaacacga ttaaaaaatg ggccagagac cctaacagat acctcaccaa     900
agatatacag atggcaatat gcatatgaaa agatgctcca taccatatgt caacagggag     960
atacaaatga aaacatcagt gagatgctat cacatctctt agaatgacca aaatctggaa    1020
cactgataac atgaatactg gcaagagtgt agagtaatag gaaatcatat acatttctga    1080
taggaattca aaatactaca gtcatcttgg aagacagttg ccagttctta caaaactaaa    1140
ctaaagatac tcttaccgtt caatccagca atcacaacct ttggtattta ctcaaaggag    1200
gtgagaactt atgtcctata aaacctgcac acagatgttt atgataactt tactcatcat    1260
ttccaaaact tgcaataacc aagatgtcct tcagtgagtg aatggacaga tcaactatgc    1320
tacatccagg caattgaata ttatttaata ctaaaaagaa atcagctacc aagcatgaat    1380
tacgtggaag aaccttaaat atgcattact aagtgaaaga agtcaatctg agaaggctac    1440
atactgtatg attccaaggg tcatggcttg aaaaagagac tgacctcaaa agagccacga    1500
gacaacattt aaagtaatag aatgttctgt atctattttg gtgatagtta catgactgcc    1560
atatttgtca aaactcatca aattgtacat ctaaaataga tgcctttatc atatgtgatt    1620
ccatctcaaa gctgccttca aaactcaagc catctacatc catattgtag tcaagtaaga    1680
aggatgctgt gaaccagaga gtagcaaaat ttttctgtaa aggacctgac ggtgaatgtt    1740
ttacttttga atgtatgtct atagcctgtc acaactgctg gactctgtct tggtaacatc    1800
aaagcaggta tagacaacag gttgaatgaa taggtgtggc tgtgtttcaa taaaacttag    1860
ttttaaacgc tgaaatttac atttcatctt tctcataagt catgaaatat tattcttcct    1920
```

```
ctgactttt  ccccaaata  atttacaaat  gtgagacact  ctcttagcta  gcaggctatc  1980
caaaaacaga  tgatagacca  gatttgatcc  acaggttgta  gtttgccaac  tcctctaaca  2040
aatgttagta  aaaaatacaa  caattatcgt  aactgtatca  tagaagtagg  atgcgggtga  2100
aacatcgata  ttccattcat  ggttacatgt  tggagatctg  tgtagactag  aaataacaag  2160
ctccattttt  cacatattct  tcaatagtac  aattttgttt  gctatgtcat  attactttgg  2220
agtagtaggc  ttaaaaaaat  caaggcgttc  ccactgtgtg  ctccaacgag  gagccatgaa  2280
gatgtggttg  tgagccctgg  tctcactcag  tgggtgaagg  atccagtatt  gccgtgagct  2340
gtagtgtaga  tatatttata  tgtgatttgc  tgaatgaata  gtccgggctt  tacaaaagaa  2400
gacaccttca  tgggaacatc  acctaacaac  tgccatagaa  gtgaccccaa  attagcgaga  2460
accattgtcc  tgagacaccc  aaggatggtg  ggagaaaaca  ccattcacac  cagctggcgg  2520
gcccagccag  tcaggaaaga  ggactgatcc  cactcagggg  gtggggtatc  acagaccccg  2580
agaacccta   aggggaagat  cttccctttg  gcaaatacat  cctacaaggt  tttgagcaat  2640
tgtcaaaatg  gagaactttt  agtaaccatg  ccttccattg  aaaaagtcat  ggccatttgt  2700
cttctttcc   ttcacttaac  tcctttcgaa  tattttcttg  ttgaaatgct  tgtaaataga  2760
aagggcagat  tctttagtgg  gagggtattt  cccaggttcc  ggagaagttg  tctgagggaa  2820
gaagagtgtg  cttgattcca  gaaggcaagt  caaggcttct  gagttacaga  tgcccaaagc  2880
acaagaactg  taatacagca  tatttcttca  taaagcccat  tctgctgtct  cagggctgca  2940
gtgtcaaatc  gtagaaacct  atgtctttga  agttcttgac  atataatgtt  gacattttca  3000
gcctctcaag  tgtatgatga  aagattagaa  tgatggtggt  gaacaagaat  gacctataga  3060
aagacatttt  ctgaagcggt  aaaaaaaacg  ttttttttt   tttaatggat  ggagaatttt  3120
tcttttgaac  tgtgagttga  ccatgaaggg  aaaaaaaaaa  tggaaagaaa  agaaagaaaa  3180
cagatcaaag  caacataaaa  attggtttta  atttctta    caaatcttg   tgggaacaaa  3240
caaatacaac  atctttttg   ttttgttttg  ttttgttttg  ggggggggg   catgcccata  3300
gcatgcaaaa  gttcctgggc  caggaatga   actatgccac  tgcagtgaaa  actgctggat  3360
ctttaaccac  taggccacca  gagaatctca  acaaatacaa  actttgagca  aatttgtgtt  3420
tgaaacatat  tcctttcttg  ccacgtagta  gaaagtattt  tcatgtgaaa  aatagtgtct  3480
atattttcct  agtacttaag  aattttgtcc  agggaatgcc  cgtagtgact  catcagtaac  3540
gaaccctact  agtatccatg  aggatgtggg  ttcaatccct  ggcctcactc  agtaggttaa  3600
ggatcccggc  tttgctgtgg  ctgtggtgta  ggctggcagc  tgtagctctg  attcgacccc  3660
tgccctgaga  acttccatat  gccacaggtg  tggctctaca  gaaaaagaaa  aaagaattgt  3720
gtccaaatga  ttctggtgtt  gtcacataaa  gatcagagct  ggaccaagtt  tgaattcaaa  3780
ggttgttgtc  taaatatttg  ttgggataaa  ttgggaatcg  gaattaacat  atacatacta  3840
ctacataaaa  aacagctaag  caaaaaaaag  aacctactat  agagcacagg  ggactttatt  3900
tagtacttcc  aaataaccta  tagtggacaa  taatatgaaa  aaatacatat  atacctgaat  3960
caccttgctg  tacacagtaa  tacaacattg  caaatcaact  atacttcaat  ttaaaaggaa  4020
ataaaaataa  aatatttaa   aaattcttgt  tcttactctt  gggcttgaaa  gagaacatta  4080
atgaggagtt  cccattgtgg  tacagtgaaa  agaatctga   ctaggaacca  tgaggttgca  4140
ggttcgatcc  ctggcctcgc  tcagtaggtt  aaggatccgg  catcgccatg  agctgtgctg  4200
ggagtctcag  atgtggcttg  gatcctgtgt  tgctgtggct  gtggtgttgg  ccaccagctg  4260
tagatctgat  tcaaccccta  gcctgggaac  ctccatatgc  cacaggtgca  gccctaaaaa  4320
```

-continued

```
gcaaaaaaaa nnnnnnnnnn nnnnnnnnga gagagagaga gagagagaga gggagaacat    4380
taatgagttc cctcgctctc cctgactctc tctctctctc attccctgtc tttgctatgt    4440
atgatattta cttgaatcta aaacatatat tttttgcat  cttaatgtgt ctgaattcag    4500
aatatcttat aatgcatggt gtctctcaat tacactcatc agcaattttt ctttctttgt    4560
ggtacataaa ataatattga atctcatagt tgatattgtc taagagtcca tgaaattaga    4620
tatacatga                                                           4629
```

METHODS

This application is a 371 of PCT/GB02/01875, filed 24 Apr. 2002, which claims priority under 35 U.S.C. 119(a)-(d) to application GB 0110036.1, filed 24 Apr. 2001.

The present invention relates to methods for genotyping pigs, such that dominant KIT allelles can be distinguished. Kits for use in such methods are also provided.

There has been an obvious selection for white colored domestic pigs since medieval time (Wiseman 1986). White pigs with pigment spots are usually eliminated from breeding in white breeds like Landrace and Large White. Despite a strong selection for white color for at least 100 years breeders have not been able to completely fix the desired phenotype, white coat without pigment spots. The inheritance of the dominant white coat color in pigs has been investigated in an intercross between the European Wild Boar and Large White domestic pigs (Johansson et al. 1992; Johansson Moller et al. 1996; Marklund et al. 1998). These investigations revealed that the dominant white phenotype is caused by two mutations in KIT, one duplication of the entire coding sequence and one splice mutation.

KIT encodes the mast/stem cell growth factor receptor. Normal expression of KIT and its ligand—the mast/stem cell growth factor (MGF)—are essential for migration and survival of neural crest-derived melanocyte precursors. Mutations in this gene cause pigmentation disorders in mice, called Dominant white spotting/w (Chabot et al. 1988; Geissler et al. 1988), and in humans, called piebald trait (Fleischmann et al. 1991; Giebel et al. 1991). Structural KIT mutations in mice are often lethal or sublethal in the homozygous form and exhibit pleiotropic effects on the development of melanocytes, hematopoietic cells, primordial germ cells, interstitial cells in the small intestine, and may affect hearing.

Four alleles have so far been identified at the porcine Dominant white/KIT locus: the recessive i allele for normal color, the semidominant $I^P$ allele for the Patch phenotype, the fully dominant I allele for the Dominant white phenotype and $I^{Be}$ for the dominant Belt phenotype. The Patch phenotype has white and fully colored patches separated by sharp borders. It has been shown that the I and $I^P$ alleles are both associated with a duplication of KIT (Johansson Moller et al. 1996; and WO97/05278). The size of the duplication is about 400 kb and includes the complete coding sequence. The duplication is most likely a regulatory mutation. This could be a simple dosage effect due to the expression of two gene copies or that the duplicated copy lacks some regulatory elements and is dysregulated. The altered KIT expression may affect ligand availability, which in turn disturbs the migration of melanocyte precursors. The high sequence identity between the two KIT copies (>99%) is consistent with the duplication being a recent event, which is likely to have occurred after domestication (Marklund et al. 1998). In addition to the duplication, the I allele has a splice mutation—a G to A substitution—in the first nucleotide of intron 17 in one KIT copy (Marklund et al. 1998; and WO99/20795). This splice mutation disrupts the highly conserved GT dinucleotide at the 5' splice site, leading to skipping of exon 17, and is therefore a structural mutation. Exon 17 encodes 41 amino acids of a highly conserved region of tyrosine kinases, comprising the catalytic loop and parts of the activation loop (Hubbard et al. 1994). There is clear evidence that the receptor form with splice mutation is expressed in a variety of cells in white pig embryos and we assume that this mutant receptor has normal ligand binding but absent tyrosine kinase activity (Marklund et al. 1998). A reduced number of white blood cells in I/I homozygous pigs was also observed suggesting mild pleiotropic effects on hematopoiesis. The Belt phenotype constitutes a white belt across the shoulders and forelegs. The $I^{Be}$ allele does not contain the duplication or the splice mutation, and no suggestive causative mutation was identified by sequencing the entire coding sequence (Giuffra et al. 1999). We assume that Belt is due to a regulatory KIT mutation.

It is difficult to genotype the KIT locus in pigs since the only known difference between some genotypes is quantitative rather than qualitative. The difference between the $I/I^P$, I/i, and I/I genotypes is that the ratio between the splice mutation and the normal form at the first nucleotide of intron 17, is 25%, 33%, and 50%, respectively. We have now quantified the ratio of the wild type/mutant nucleotide at the splice site, utilising pyrosequencing (Ronaghi et al. 1998) and minisequencing (Syvanen et al. 1993). The minisequencing assay has previously been applied to distinguish between one, two, and three copies of an allele on human chromosome 4 (Laan et al. 1995) and to accurately quantify alleles present in ratios ranging from 1% to 99% in pooled DNA samples (Olsson et al. 2000).

As a result of this work we have now determined that a number of dominant white alleles exist at the KIT locus. Thus, in a first aspect the present invention provides a method of determining the KIT genotype of a pig which comprises:—

(i) obtaining a sample of pig nucleic acid; and
(ii) analysing the nucleic acid obtained in (i) to quantify the percentage of splice variant copies of the KIT gene present.

Thus, on the basis of a relatively simple quantitative analysis of the KIT gene various coat colour genotypes can be determined. Thus, the predicted genotypes vs % splice would be as follows:

| Genotypes | % of splice[a] |
|---|---|
| i, $I^{Be}$, $I^P$ [b] | 0 |
| $I^2/I^P$ | 20 |
| $I^2/i$, $I^2/I^{Be}$, $I^1/I^P$ | 25 |
| $I^1/i$, $I^1/I^{Be}$, $I^2/I^2$ | 33 |
| $I^1/I^2$, $I^3/I^P$ | 40 |
| $I^1/I^1$, $I^3/i$, $I^3/I^{Be}$, $I^2/I^3$ | 50 |
| $I^1/I^3$ | 60 |
| $I^3/I^3$ [c] | 66 |

[a] % splice = (number of copies with the splice variant/total gene copy number) × 100.
[b] All possible genotype combinations of these alleles.

Suitably, the determination in (ii) is carried out using minisequencing and/or pyrosequencing techniques as described herein.

In addition, we have also looked at the KIT gene sequence and have determined that there is a unique sequence at the boundary between duplicated KIT genes. We have labelled this the "duplication breakpoint". Thus, in a second aspect, the present invention provides a method of determining the KIT genotype of a pig which comprises:—

(i) obtaining a sample of pig nucleic acid; and
(ii) analysing the nucleic acid obtained in (i) to identify the presence or absence of one or more copies of the duplication breakpoint.

As discussed in Example 2, the BAC clone BAC953F11 shown in FIG. 11 represents the duplication breakpoint.

The analysis in step (ii) may be done by PCR using appropriate primers. Examples of suitable primers are given in Example 2 and include 953R2, 953F1, 953F9 and 953R3.

The duplication of the KIT gene results in a unique sequence at the boundary between the duplicated sequences. This sequence is also present in alleles containing more than two copies of KIT (e.g. $I^2$ and $I^3$). This sequence can therefore be used as a dominant marker to identify animals (or samples derived from them) that contain at least one copy of alleles with increased copies of KIT.

Samples that are ii or $I^{Be}I^{Be}$ or $iI^{Be}$ do not contain this duplication, whereas the alleles F, $I^1$, $I^2$ and $I^3$ all contain the boundary sequence.

This sequence can be used alone or in combination with other breed specific markers as part of traceability systems based on breed. For example, this sequence can be used to check the integrity of Large White populations.

The Pietrain (as well as Large White and Landrace breeds) and Berkshire breeds both contain the same allele at the extension locus (MC1R gene, allele Ep) so that the MC1R locus cannot be utilised to distinguish these two breeds. However, Berkshire samples can easily be distinguished from Pietrain using a test for this sequence: Berkshire does not contain the unique boundary sequence whilst Pietrain animals will be positive for the sequence.

In some markets meat from the Berkshire breed is sought after, so that Berkshire carcasses and meat is sold at a premium. In this situation, it is advantageous to be able to test meat to confirm its origin. Samples that are homozygous for the MC1R Ep allele could be from Pietrain, Large White, Landrace or Berkshire animals, however, samples from the Berkshire breed will be the only ones not positive for the boundary sequence.

Suitably, the methods of the first and second aspects find use in determining coat colour genotype. The methods may be used in conduction with the methods described in, for example, WO 97/05278 or WO 99/20795. In addition, these methods allow breed determination, by distinguishing breeds on the basis of KIT genotype. The present methods are another way to increase confidence in breed determination described in, for example, WO 98/54360.

Furthermore, the methods of the first and second aspects find us in screening pigs to determine those more likely to produce larger litters, and/or those less likely to produce larger litters.

In addition the methods of the present invention can also be used for selecting animals for preferred performance for other economic traits which vary according to KIT genotype The ability to fully characterise the different KIT alleles (both copy number and KIT variation/polymorphism) provides the basis to maintain the optimal KIT genotype in both breeding lines and in the multiplication of these breeds or lines and production of parent boars and gilts.

For example, a breeding company can screen each generation of animals to ensure that those selected to produce the next generation are of the preferred KIT genotype.

In this way variation at the KIT locus will be reduced so as, ultimately, to reduce the incidence of coloured slaughter pigs. Animals can be screened at different levels of the multiplication/production pyramid depending on allele frequency. In some situations it may be necessary to screen female pigs produced as parent gilts (females sold for the production of slaughter pigs) to ensure that they are of the desired genotype. The invention will allow this screening to be achieved at birth in order to identify any recombination events generating the undesirable alleles.

Selection against the different KIT alleles using the invention will also have the benefit of reducing the frequency of deleterious alleles that may have negative pleiotropic effects on performance. The KIT gene product is involved in many different developmental processes and is particularly associated with ovulation, embryogenesis and hematopoiesis, so that the generation of new KIT alleles (e.g. higher copy numbers of KI2 or KI3), may result in reduced fertility, immune response and/or survival.

The present invention provides new methods for genotyping the duplication breakpoint and the quantification of KIT sequences (wild type and splice mutation) providing the means to screen effectively for the different alleles at the pig KIT locus.

As it is now possible to differentiate the different KIT alleles and their combinations (including alleles with more than three copies of the KIT locus), the invention will allow the pleiotropic effects of the alleles to be determined. It will then be possible to select for the optimal alleles for different lines or breeds and different uses.

Thus, the data described herein indicates that there is substantial allelic variation at the KIT locus.

The preferred dominant white genotype for this population is $I^1/I^1$, which has the ratio 50%. The frequency of this ratio is approximately 0.5. However, this will be an overestimate of the frequency of allele $I^1$ as it is clear that additional alleles are present in the population and other allelic combinations give a ratio of 50%.

In order to select for this genotype, a population is genotyped and animals are selected with a ratio of splice/wild type sequence of 0.5 to select the parents for the next generation. The animals selected are likely to contain undesirable alleles, i, $I^{Be}$, $I^2$ and $I^3$. Offspring from selected animals are then screened for their KIT ratio in order to detect the undesirable alleles. In this way all of the undesirable alleles can be detected over time, depending on their frequency, for example:

Generation 1—prospective animals to be selected as parents for Generation 2. Animals containing 50% KIT splice may be; $I^3/i$, $I^3/I^{Be}$, $I^2/I^3$ and $I^1/I^1$. These alleles have the following structure KIT/Splice (see FIG. 2)

| | |
|---|---|
| i and $I^{Be}$ | 1/0 |
| $I^1$ | 2/1 |
| $I^2$ | 3/1 |
| $I^3$ | 3/2 |

Generation 2—progeny from the selected parents are screened for KIT/splice ratio.

Offspring from two parents with the $I^1/I^1$ genotype will all have the ratio 0.5 as both alleles are 2/1.

Offspring from parents with other genotype combinations will have variable ratios.

For example, a cross between a boar with the genotype $I^1/I^1$ and a sow with the genotype $I^3/i$, will generate offspring with $I^1/I^3$ (2/1+3/2=5/3=0.6) and $I^1/i$ (2/1+1/0=3/1=0.33).

Furthermore, a cross between a boar with the genotype $I^1/I^1$ and a sow with the genotype $I^2/I^3$, will generate offspring with $I^1/I^2$ (2/1+3/1=5/2=0.4) and $I^1/I^3$ (2/1+3/2=5/3=0.6).

A third method for the determination of the structure of the KIT gene is to use a linked genetic polymorphism which is closely associated with the presence or absence of the duplication. Such a polymorphism may occur in the KIT gene itself or in a chromosomal region linked to KIT. By using a single linked marker in complete association with the presence/absence of the duplication or a combination of markers showing a partial association a highly informative test can be developed. For instance, the SSCP (Single Strand Conformation Polymorphism) method may be used to develop such polymorphism. The principle of the method is that double-stranded DNA, produced by PCR, is denatured into single-stranded DNA which is then separated by non-denaturating gel electrophoresis. Under non-denaturating conditions the single-stranded DNA forms a secondary structure due to intrastrand interaction but a proportion of the single-stranded DNA will rename and form double-stranded DNA. Two types of polymorphism may be revealed by this method Firstly, a difference in nucleotide sequence between two alleles may influence the secondary structure of single-stranded DNA which is revealed as a difference in the mobility rate during electrophoresis. Secondly, a difference in nucleotide sequence often influences the mobility of the heteroduplex DNA (A heteroduplex is a double-stranded DNA molecule formed by two single-stranded molecules representing different alleles).

Another method of determining the structure of the KIT gene in relation to the number of copies of the region subject to duplication involves the use of pulsed field gel electrophoresis. Pulsed field gel electrophoresis being a technique in which the size of large DNA fragments can be analysed. In this application the process would be to utilize a restriction endonuclease that cleaved the genomic DNA at specific sites flanking the region found to be duplicated in the DNA of animals carrying the I allele of the KIT gene. Genomic DNA cleaved with such an enzyme would be subject to pulsed field electrophoresis followed by transfer to a DNA binding membrane. A probe specific for the region subject to duplication could then be used to determine the original location on the gel, and therefore the size of that fragment by comparison to suitable DNA size standards. Should the DNA from an animal contain a duplication of a portion of the KIT gene, this specific fragment would be increased in size. Heterozygous animals will be found to show two differently sized specific bands, the smaller representing the non duplicated allele i, the, larger representing the duplicated allele I or $I^P$. This technique will also show alleles containing more than two copies of the duplicated region through the presence of fragments having a further increase in size by the unit length of the duplication.

Association between genetic markers and genes responsible for a particular trait can be disrupted by genetic recombination. Thus, the closer the physical distance between the marker and the gene in question, the less likely it is that recombination will separate them.

It is also possible to establish linkage between specific alleles of alternative DNA markers and alleles of DNA markers known to be associated with a particular gene (e.g. the KIT gene discussed herein), which have previously been shown to be associated with a particular trait. Thus, in the present situation, taking the KIT gene, it would be possible, at least in the short term, to select for pigs with a particular coat colour, indirectly, by selecting for certain alleles of a KIT gene associated marker through the selection of specific alleles of alternative chromosome 8 markers. Examples of such markers known to be linked to the KIT gene on porcine chromosome 8 include genetic polymorphism in the KIT gene itself or in the closely linked genes for the α-subunit of platelet derived growth factor (PDGFRA) and albumin.

Particular genetic markers associated with the KIT gene are microsatellites. These are simple sequence repeats of 4, 3 or, more usually, 2 nucleotides, which occur essentially at random around the genome at approximately every 50,000 bases (about 60,000 microsatellites per haploid genome). Stuttering of DNA polymerase during replication and unequal crossing-over during recombination are thought to result in the loss or gain of repeat units. This means that microsatellites are usually polymorphic and can have several repeat length alleles.

Examples of linked microsatellite sequences include S0086, S0017 (Coppieters et al, Animal Genetics 24: 163-170 (1993)), Sw527, Swr750 and SW916. It would be possible to select indirectly for alleles of the KIT gene linked to coat colour using any of the above markers, or indeed any other linked markers on porcine chromosome 8.

Thus in a further aspect, the present invention provides a method for determining the KIT genotype of a pig which comprises determining the presence of at least allele associated with at least one DNA marker linked either directly or indirectly to KIT. Suitably, the DNA marker may be a microsatellite. In particular the DNA marker may be S0086, S0017, Sw527, Swr750 or SW916 As with the first and second aspects, this method can be used to determine coat colour genotype, for breed determination, and for screening pigs to determine those more likely to produce larger lifters, and/or those less likely to produce larger litters.

As discussed herein, the present invention relies upon a determination of KIT gene DNA sequence copy number. To that end a nucleotide probe representing the duplicated KIT segment, or part of it or indeed any other nucleotide probe showing sufficient similarity to such a porcine probe may be used. For example, the following methods can be used to carry out such a determination:

(i) using nucleotide probes derived from nucleotide sequences of at least part of the DNA of the KIT gene, and RNA derived from it, from, e.g. mouse (Gokkel et al, *Oncogene* 7, 1423-1429 (1992)) and/or man (Giebel et al, *Oncogene* 7, 2207-2217 (1992)). Such probes, due to conservation, would hybridise to the pig gene;

(ii) where the amino acid sequence of the KIT protein of an animal is known, the possible nucleotide sequences of the DNA encoding that protein, or portions of it, can be deduced. Based on that, mixed oligonucleotide preparations can be used as probes for the pig KIT gene;

(iii) probes can be designed based on the protein sequences (and corresponding nucleotide sequences) for proteins that have functional homologies to the whole or part of the KIT gene, for example v-KIT (Besmer et al, *Nature* 320: 415-421 (1986)).

All of the probes derived as described above may be used to probe animal derived nucleic acid preparations transferred to suitable matrices for hybridisation such as Nylon membranes (e.g. Hybond N Amersham International) by Southern, northern or dot blotting. The ratio of the amounts of the KIT and control probes hybridising to the matrix bound nucleic acid can be used to determine KIT copy numbers. The amount of bound probes can be quantified through labelling the probes with radioactive isotopes. Other, non-isotopic nucleic acid labelling kits are now available and can also be used.

The reverse of the procedure involving hybridisation of animal derived nucleic acid to matrix is also possible. In this, probe is bound to the matrix and used to capture, through a hybridisation protocol, genomic DNA or RNA labelled in such a way as previously described, thus allowing quantitation of the amount bound. The amount bound is, if the conditions are correct, related to the total amounts (or copy number) of the KIT and control nucleic acid sequences present.

Other methods of quantifying PCR amplified DNA include radiolabelling based methods. An example is radiolabelling of one or both of the oligonucleotide primers, followed by quantitation of the radioactivity in the PCR product through densitometry of autoradiographs of DNA gels. An alternative procedure is the differential labelling of the oligonucleotides for the two products of the PCR reaction with different isotopes allowing quantification of each separate product after removal of unincorporated labelled oligonucleotides through precipitation, filtration, differential centrifugation or other procedures. PCR product can also be quantitated using other staining procedures utilising dyes such as ethidium bromide or SYBR green Molecular Probes, Inc.) in combination with densitometry or fluorimetry.

Yet another method of quantifying the products of a differential PCR in which two PCRs proceed in the same tube to produce two separate products, as described in this patent, is the use of the TaqMan™ system (Perkin Elmer Corp.). In this system, in addition to the two oligonucleotide primers flanking the region to be amplified a third oligonucleotide probe is used that binds to the amplified region. The flanking primers are unlabelled while the probe carries two fluorescent labels. On the 3' end of the probe is a reporter dye, the fluoresence of which is quenched by a separate fluorophore attached to the 5' end of the probe. During PCR this probe binds to the product DNA molecules. As PCR proceeds these products are used as templates during which the Taq DNA polymerase cleaves off the 5' quenching dye of the probe as it displaces it. This removal of the quenching agent allows fluoresence from the reporter dye to be detected. The degree of fluoresence is proportional to, and therefore a measure of, the amount of PCR product produced. A reaction may include two separate sets of PCR primers and two probes, each corresponding to a separate genomic DNA region. In this way, as long as the criteria for quantitative PCR are obeyed, the relative amounts of each template region can be measured.

A kit can be prepared to carry out the methods described herein. These kits may comprise one or more containers filled with one or more well known reagents for carrying out PCR, minisequencing, or pyrosequencing techniques. A kit for quantifying the percentage of splice variant copies of the KIT gene present, by minisequencing or pyrosequencing methods may include well know reagents utilized in these techniques, such as nucleotide triphosphates (dATP, dCTP, dGTP, dTTP), enzyme mixtures (DNA polymerase, ATP sulfurylase, luciferase and apyrase), substrate mixtures (APS and luciferin), and instructions for their use. The enzyme and substrate mixtures can be provided as individual components or a ready prepared mixture. In addition these kits may also include a primer, for example 5'-TAATT-TACNTGGTCAAAGGAAAC-3', N=inosine (SEQ ID NO: 17).

A kit for determining the KIT genotype utilizing PCR techniques may include reagents such as a DNA polymerase, suitable buffers, nucleotide triphosphates, oligonucleotide primers and instructions for their use.

Some of the nucleotide triphosphates may further incorporate a label, which may be radioactive, fluorescent or a protein, such as an enzyme or biotin for example dATPαS.

The reagents may be in provided in a freeze-dried or lyophilised form or as a ready made solution. Such kits may also include other containers or devices for utilising the kit, and written instructions.

The oligonucleotide primers supplied with the kit would be suitable for determining the KIT genotype of a pig. In particular one or more of the following pairings of oligonucleotides could be used:

```
5'-GTATTCACAGAGACTTGGCGGC-3'     (SEQ ID NO: 1)
and
5'-AAACCTGCAAGGAAAATCCTTCACGG-3' (SEQ ID NO: 2)

5'-CTACCTTTGCCATACCATGCATTT-3'   (SEQ ID NO: 3)
and
5'-TTGCATGCCCTCTAATTACACAATT-3'  (SEQ ID NO: 4)

5'-CCACAATATACCTA CAGAATTAC-3'   (SEQ ID NO: 5)
and
5'-AACCTGTGGATCAAATCTGGT C-3'    (SEQ ID NO: 6)

5'-GTTCAATCCAGCAATCACAAC C-3'    (SEQ ID NO: 7)
and
5'-AACCTGTGGATCAAATCTGGT C-3'    (SEQ ID NO: 8)

5'-GTTCAATCCAGCAATCACAAC C-3'    (SEQ ID NO: 9)
and
5'-TTTTAATCCTCTTAAGGACCAAC-3'    (SEQ ID NO: 10)

5'-TAA GTG AAA GAA GTC AAT CTG AG-3' (SEQ ID NO: 11)
and
5'-GGC AGT CAT GTA ACT ATC ACC-3' (SEQ ID NO: 12)
```

Figure 2:
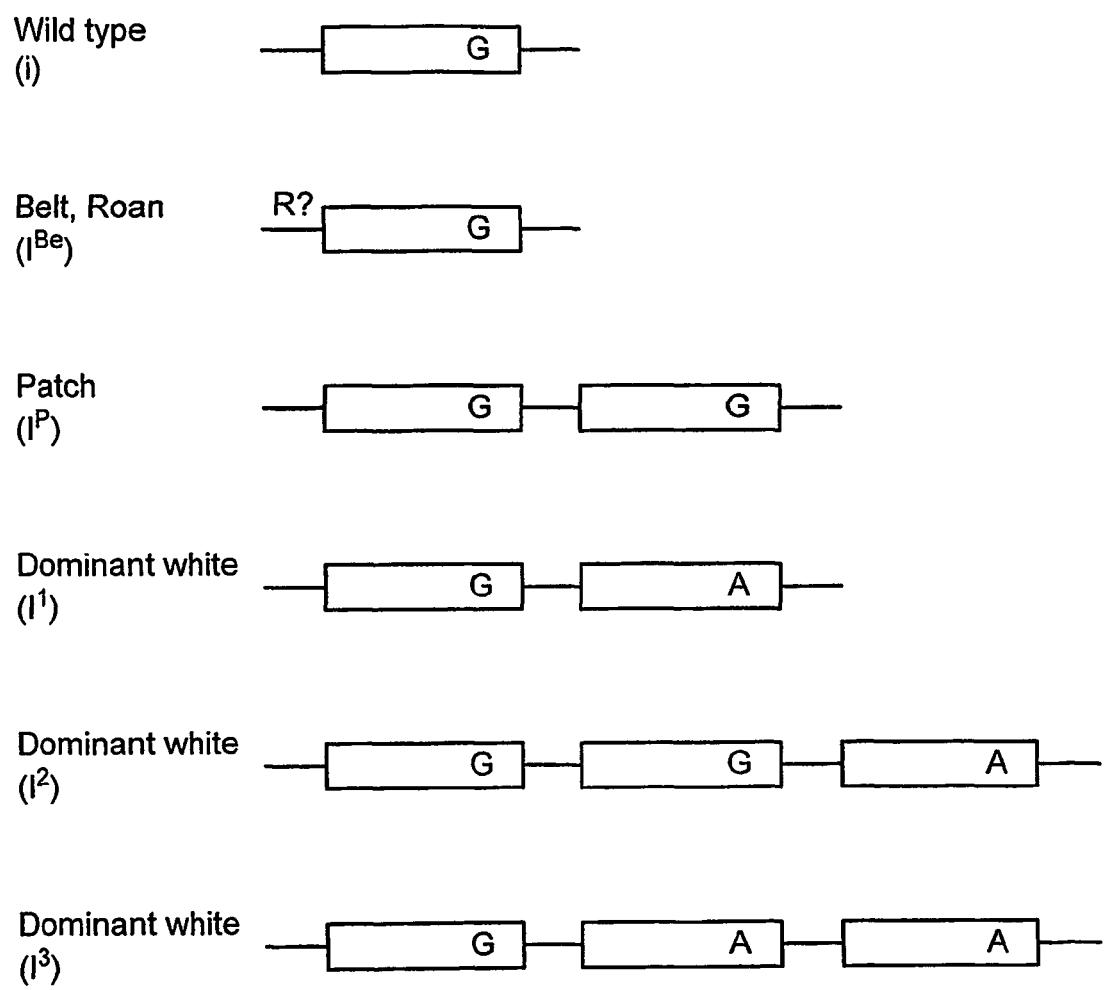
Figure 3:
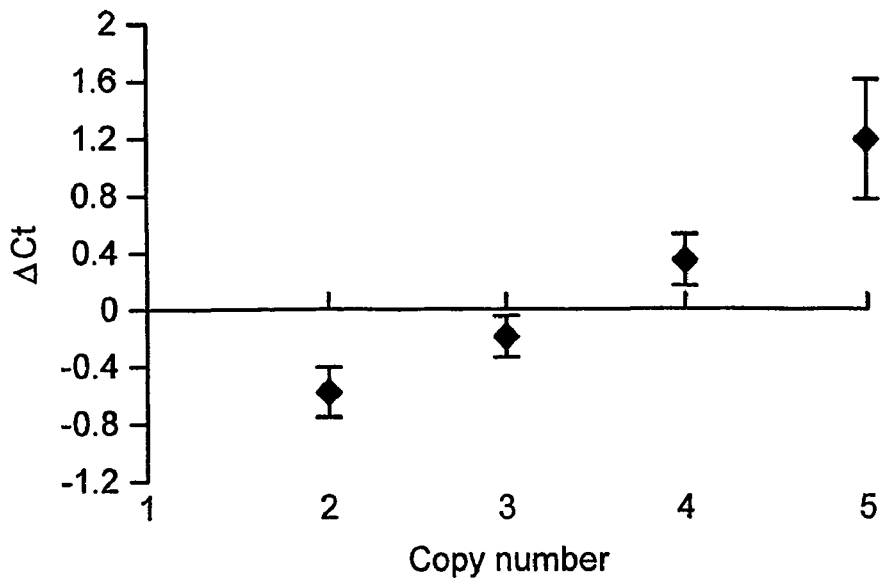
Figure 4:
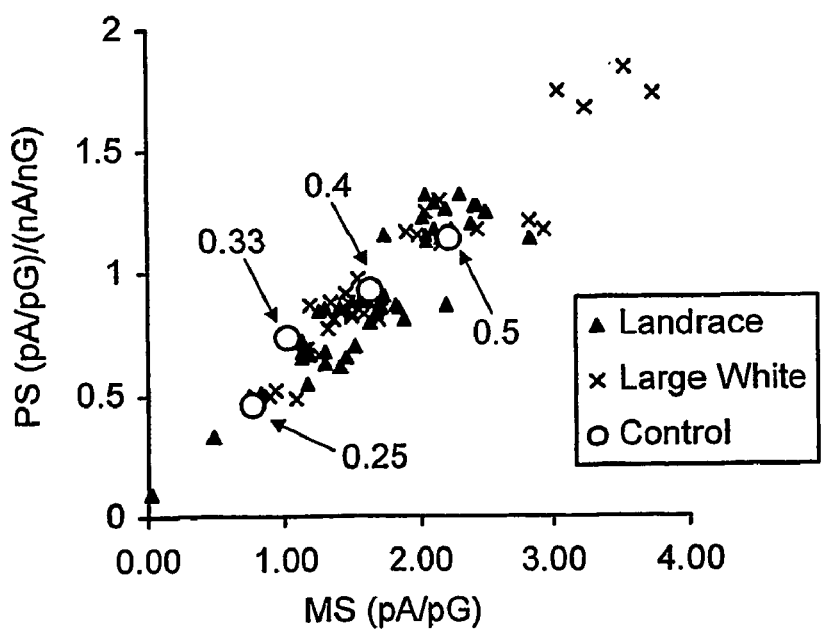
Figure 5A:
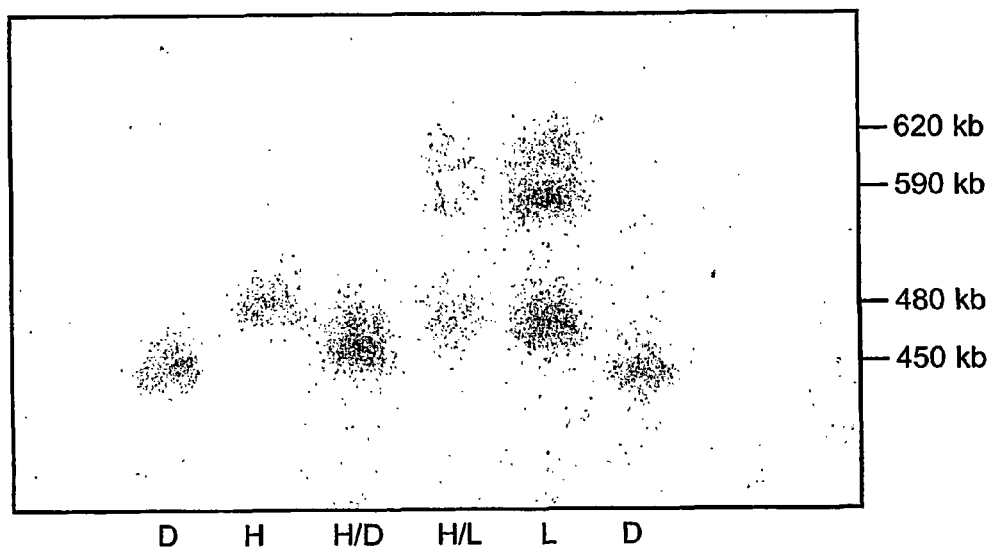
Figure 6:
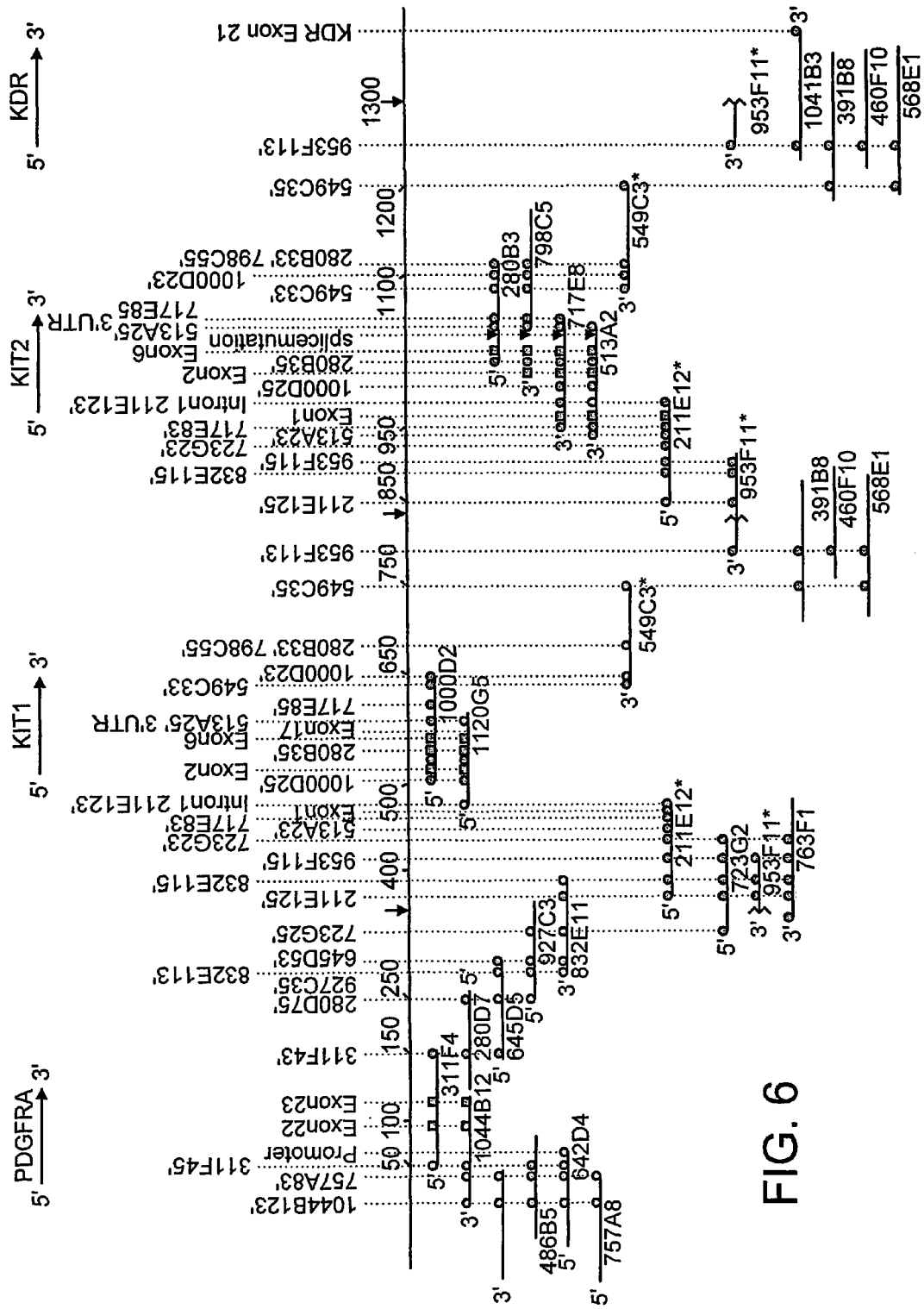

The invention will now be described with reference to the following examples, which should not be construed as limiting the scope of the invention. The examples refer to the figures in which:

FIG. 1: Quantitative analysis estimating the ratio of splice mutation (pA) to normal (pG) at the first nucleotide of intron 17 in the KIT gene using pyrosequencing (PS) and minisequencing (MS) in a Wild Boar/Large White intercross. In case of pyrosequencing the ratio pA/pG was standardised by the ratio of the next A (nA) and next G (nG) in the sequence. (A) The founder animals (W1-W10), n=10. (B) $F_1$ animals, n=23. (C) $F_2$ animals, n=178. The symbols represent the estimated ratio for the splice mutation; ? in FIG. 1C implies that it was not possibly to unambiguously deduce the splice ratio based on pedigree data;

FIG. 2: Schematic description of Dominant white/KIT alleles in the pig. The duplication is about 400 kb. G and A reflect the normal and splice mutation, respectively, at nucleotide 1 in intron 17. R(?) indicates that we have postulated that the Belt allele is due to a regulatory mutation. It is possible that the Belt and Roan phenotypes are controlled by different alleles both containing a single copy of KIT without the splice mutation (see text). We have not observed the phenotype associated with the $I^3$ allele but it is most likely Dominant white;

FIG. 3: Relative quantification of genomic copy numbers of KIT using ESR (the estrogen receptor gene) as a single copy control. The material comprises a European Wild Boar/Large White intercross: founders, n=10; $F_1$, n=23; $F_2$, n=178. The X-axis represents the predicted copy number using the quantification of the splice mutation and family segregation analysis. The Y-axis represents the Ct(ESR)-Ct (KIT) reflecting the relative difference in copy number of KIT and ESR in S genomic DNA samples. The data points are ΔCt±SE;

FIG. 4: Quantitative analysis estimating the ratio of splice mutation (PA) to normal (pG) at the first nucleotide of intron 17 in the KT gene using pyrosequencing (PS) and minisequencing (MS) in commercial populations of white Landrace and Large White pigs: Landrace, n=48; Large White, n=33. The controls are from the European Wild Boar/Large White intercross and the ratio of the splice form has been deduced with great confidence for these animals;

FIG. 5: Results of PFGE analysis of the PDGFRA-KIT-KDR region in pigs (A.) Southern blot analysis of NarI digested genomic DNA hybridized to a KT intron 18 probe. Samples from Duroc (D) KIT-i/i, Hampshire (H) KIT-$I^{Be}$/$I^{Be}$, Large White (LW) KIT-I/I, a Duroc/Hampshire crossbred animal, and a Hampshire/Large white crossbred animal were used. The estimated sizes of fragments are given to the right in kilobase pairs. (B.) Schematic figure summarising the interpretation of the PFGE data. The approximate locations of the duplication breakpoints are indicated by arrows, the locations of restriction sites are indicated by vertical lines, and the locations of the gene and STS probes used for hybridization are indicated. (*) denotes that different fragments were visible in Large White animals probably due to different states of methylation at closely linked BssHII sites;

FIG. 6: Map of the BAC contig of the PDGFRA-KIT-KDR region on pig chromosome 8. The location of genes and STSs are shown; the relative order of KI2 and KI3 has not yet been determined. The orientation of the genes has so far been determined for PDGFRA, KI2, and KI3 while the orientation of KDR are given according to the one established in human (Spritz et al. 1994). The locations of the duplication breakpoints are indicated by vertical arrows. The BAC clones 211E12 and 549C3 are marked by asterisks and are present twice since it has not yet been established whether they belong to KI2 or KI3, FIG. 7: Southern blot analysis of HindIII digested BAC clones from the porcine KIT region and pig genomic DNA. (A.) BAC clones 832E11 (lane 1), 953F11 (lane 2 and 3), and 1041B3 (lane 4) hybridized with BAC DNA from clone 953$F_{11}$ from the KIT 3'-5' duplication region. The unique 3.9 kb HindIII fragment present at the duplication breakpoint is indicated. (B) Genomic Southern blot of founder animals from a Wild Boar/Large White intercross hybridized with a PCR fragment from the duplicated region. 1: W1, i/i; W2, i/i; W5, $I^1/I^2$; W6, $I^1/I^{Be}$; W7, $I^1/I^1$; W8, $I^1/I^P$. The unique 3.9 kb HindIII fragment from the duplication breakpoint is indicated. The 9.0 kb fragment was monomorphic and originates from the region represented in BAC 832E11.

Figures 7, 8:
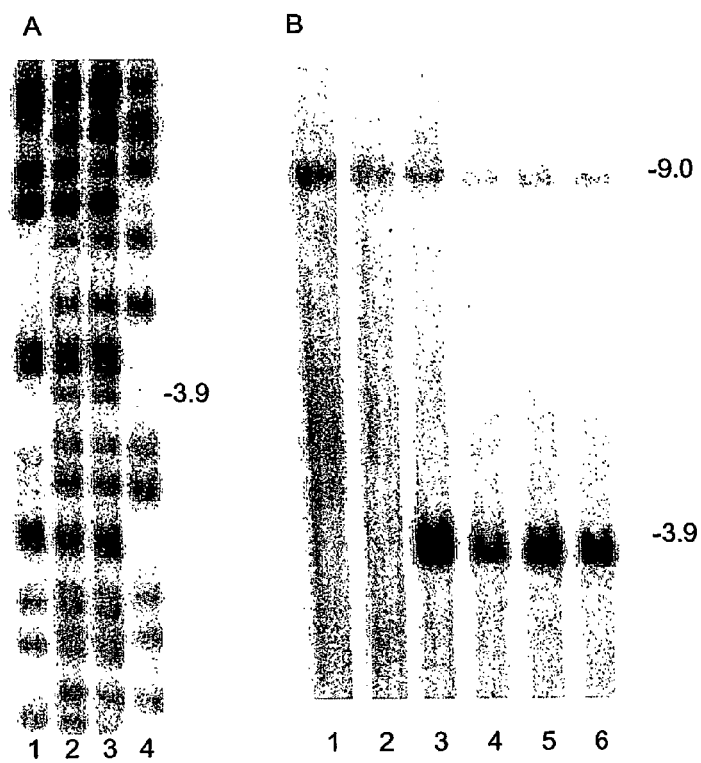

FIG. 8: Sequence comparison of part of a fragment from BAC953F11 (SEQ ID NO: 18) containing the unique duplication breakpoint associated with the KIT duplication in comparison with the corresponding regions in BACs 1041B3 (SEQ ID NO: 19) and 832E11 (SEQ ID NO: 20) containing the sequences present on non-duplicated chromosomes. A dash indicates identity to the master sequence.

FIG. 9. Sequence of BAC 1041B3 as described in Example 2 (SEQ ID NO: 21).

FIG. 10. Sequence of BAC 832E11 as described in Example 2 (SEQ ID NO: 22).

FIG. 11. Sequence of BAC 953F11 as described in Example 2 (SEQ ID NO: 23).

Figure 12:
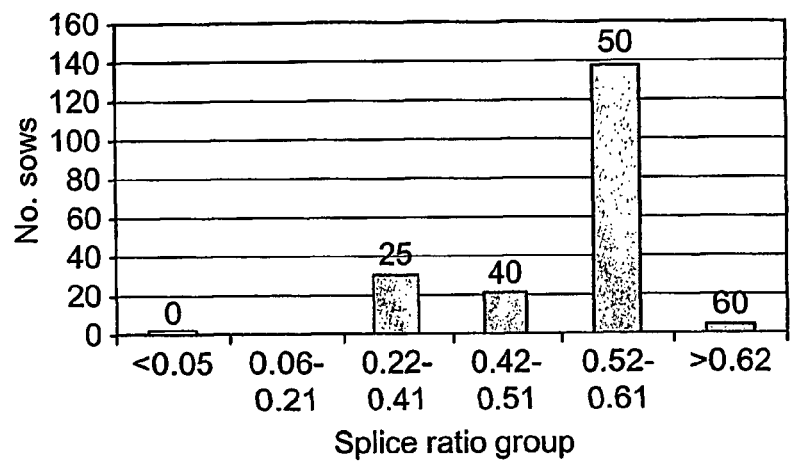

FIG. 12. Distribution of splice ratios (numbers above bars are the lab classification for % splice).

Figure 13:
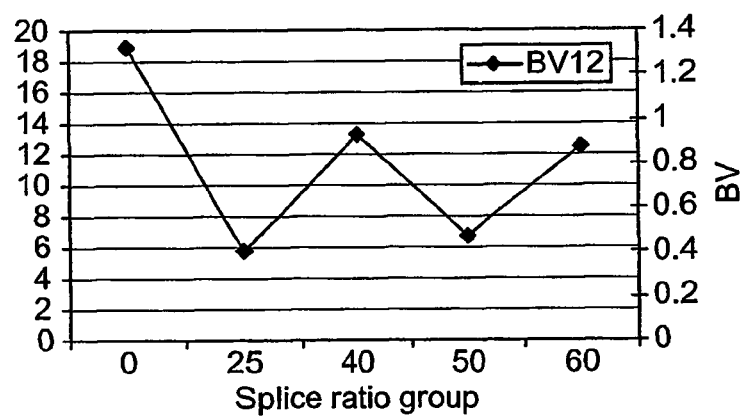

FIG. 13. LSMeans for litter size traits per splice ratio group

Figure 14:
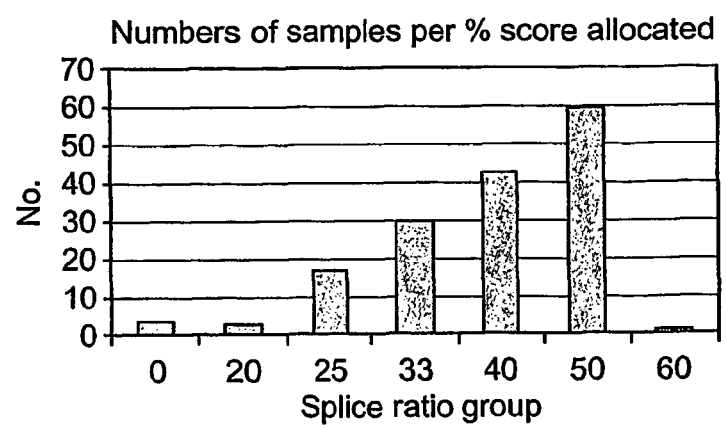

FIG. 14. Distribution of scores for the 8 white lines analysed for splice ratio.

EXAMPLE 1

Animals: An intercross pedigree comprising two European Wild Boar and eight Large White founders, 23 $F_1$, and 178 $F_2$ animals was used. This pedigree has been extensively used for studies on coat color genetics (Johansson et al. 1992; Johansson Moller et al. 1996; Mariani et al. 1996; Marklund et al. 1998; Kijas et al. 1998). The distribution of KIT alleles in commercial populations was investigated using samples of 33 Swedish Large White and 48 Swedish Landrace pigs.

PCR amplification: Parts of exon 17 and intron 17 of KIT were amplified using the PCR primers KI31 5'-GTATTCA-CAGAGACTTGGCGGC-3'(SEQ ID NO: 1) and KIT35 5'-AAACCTGCAAGGAAAATCCTTCACGG-3' (SEQ ID NO: 2) (Marklund et al. 1998). Primer KIT35 was 5'-biotinylated to allow capture of the PCR products onto avidin-coated solid supports. PCR reactions were carried out in a total volume of 50 µl containing 40 ng genomic DNA, 1.5 mM $MgCl_2$, 50 mM KCl, 10 mM Tris-HCl (pH 8.3), 200 µM dNTPs, . 1.25 U AmpliTaq Gold DNA polymerase (PE Applied Biosystems, USA) and 10 pmol of both forward and reverse primer.

Pyrosequencing: Twenty-five µl of biotinylated PCR product was immobilized onto streptavidin-coated paramagnetic beads (Dynal AS, Oslo, Norway) using Binding-Washing buffer (5 mM Tris-HCl, 1M NaCl, 0.5 mM EDTA, 0.05% Tween 20, pH 7.6) in a total volume of 90 µl at 43° C. for 30 mm. Single-stranded (ss) DNA was obtained by incubating the immobilized PCR product in 50 µl of 0.5 M NaOH for 1 mm and washing the beads once in 100 µof Binding-Washing buffer. Fifteen pmoles of detection primer KitSeq TAATTACNTGGTCAAAGGAAAC-3', N=inosine (SEQ ID NO: 17), designed with its 3' end immediately upstream of the splice mutation, was allowed to hybridize onto ssDNA in 40 µl of Annealing buffer (20 mM Tris-Acetate, 5 mM $MgAc_2$, pH 7.6) at 80° C. for 2 mm with subsequent cooling down to room temperature. Pyrosequencing was carried out using the SNP Reagent Kit containing dATPαS, dCTP, dGTP, dTTP, enzyme mixture (DNA polymerase, ATP sulfurylase, luciferase and apyrase) and substrate mixture (APS and luciferin) and the PSQ96 instrument (Pyrosequencing AB, Uppsala, Sweden). The result of the pyrosequencing assay was expressed as the ratio between the signals from the incorporated dATPαS and dGTP, standardized with the ratio of the next incorporated dATPαS and dGTP in the sequence.

Minisequencing: Four 10 µl aliquots of each PCR product were mixed with 40 µl of Binding buffer (50 mM phosphate buffer pH 7.5 containing 0.15 mM NaCl and 0.1% Tween 20) in streptavidin-coated microtiter plate wells (Combiplate 8, Labsystems, Finland) and incubated at 37° C. for 1.5 hours in a shaker (Labsystems Thermomix 1415, Finland). The wells were washed with 40 mM Tris-HCl (pH 8.8), 1 mM EDTA, 50 mM NaCl and 0.1% Tween 20 in an automatic plate washer (Wellwash Labsystems, Finland). The non-biotinylated strand of the PCR-product was removed by denaturation with 60 µl of 0.1 M NaOH for three minutes. After washing as above, 50 µl of a minisequencing reaction mix, containing DNA polymerase buffer, 0.2 U of Taq polymerase (PE Applied Biosystems, USA), 0.1 µgCi of [$^3$H]-dATP (TRK 633, 57-76 Ci/mmol) or [$^3$H]-dGTP, (TRK 627, 24-34 Ci/mmol) (Amersham Pharmacia Biotech, England) and 10 pmol of the detection primer KitSeq, was added to the wells. The plates were incubated at 50° C. for 10 min. The unincorporated label was removed by washing as above, and the sequencing primers were released with 100 µl of 0.1 M NaOH, and measured in a liquid scintillation counter (1414, Wallac, Finland). The result of the minisequencing assay is expressed as the ratio between the signals from the incorporated [$^3$H]-dATP and [$^3$H]-dGTP.

Relative quantification of KIT copy number using real-time PCR: The copy number of KIT in different genotypes was determined as previously described (Giuffra et al. 1999) using the comparative $C_T$ method based on PCR amplification of the target KIT gene and the single copy control gene (ESR, estrogen receptor gene) in separate tubes. The PCR primers for KIT were forward 5'-CTACCTTTGCCATAC-CATGCATTT-3' (SEQ ID NO: 3) and reverse 5'-TTGCAT-GCCCTCTAATTACACAATT-3' (SEQ ID NO: 4) and for ESR forward 5'-GCAGCTGCCAACCTATTCCA-3' (SEQ ID NO: 13) and reverse 5'-TGGGTTTAGGATGCAG-CATTG-3' (SEQ ID NO: 14). The PCR reaction was performed using the ABI7700 instrument (PE Applied Biosystems, USA) in 25 μl reaction volumes using the TaqMan universal PCR Master Mix (PE Applied Biosystems, USA). The KIT specific TaqMan probe 5'-TGCAAAAGCACACT-TCATCTGACGGCT-3' (SEQ ID NO: 15) was labelled with FAM at its 5'-end and the ESR specific probe 5'-CATCTG-CACCCTACACCACAGCTCACA-3' (SEQ ID NO: 16) was labelled with VIG at its 5'-end. The time and temperatures in the thermal cycling were an initial 2 min hold at 50° C. and a 10 min hold at 95° C. for AmpErase and AmpliTaq Gold activation, respectively (PB Applied Biosystems, USA) followed by 40 cycles of 15 sec at 95° C. and 1 min at 60° C. Duplicate DNA samples were tested for each animal.

Results

Segregation analysis of Dominant white/KIT alleles in the Wild Boar/Large White intercross reveals additional KIT alleles: Minisequencing and pyrosequencing were used to determine the ratio between the KIT sequence containing the splice mutation and the KIT sequence with the normal nucleotide at the first position in intron 17 in all animals in the Wild Boar/Large White intercross. The following four groups of ratios were expected: 0% splice variant (i/i, $I^P$/i), 25% (I/$I^P$), 33% (I/i), and 50% (I/I). By plotting the ratios obtained by the two methods, clusters consistent with our previous interpretation of the composition of KIT alleles in this pedigree were observed (FIG. 1). However, clear evidence for additional allelic heterogeneity was observed. The founder animals (FIG. 1A) were assigned to five different clusters: 0% splice, the two Wild Boars being i/i; 25% splice, one Large White sow (W8) being heterozygous for the Patch allele I/$I^P$; 33%, a single Large White sow (W6) being heterozygous for an allele carrying a single KIT copy and no splice mutation; 40%, three females that were heterozygous for a new allele with three KIT copies; 50%, only three out of eight Large White sows were homozygous I/I.

The interpretation that the W6 female carried a novel allele with only one copy and no splice mutation was confirmed by our observation that about half of its $F_1$ progeny and a proportion of its $F_2$ grand progeny did not carry the splice mutation at all. We can exclude that this allele is identical to the wild type allele (i) since none of the $F_2$ animals carrying this allele showed the wild type color. Since we cannot formally exclude the possibility that this allele is identical to the Belt allele ($I^{Be}$) we suggest that it is given the same allele designation until molecular characterization or informative pedigree material can reveal whether these are two distinct alleles. This allele was recessive to Dominant white since I/$I^{Be}$ heterozygotes were white. The $F_2$ animals being heterozygous $I^{Be}$/i showed two different phenotypes due to interaction with the Extension/MC1R locus segregating in this cross (see Kijas et al. 1998; Giuffra et al. 1999). $F_2$ animals with the genotype $I^{Be}$/i, $E^+$/− showed a distinct Roan phenotype characterized by white hairs intermingled with pigmented hair whereas $F_2$ animals with the genotype $I^{Be}$/i, $E^P/E^P$ were predominantly white with some black spots. Three of the Large White founder sows (W4, W5, and W10) showed a proportion of A versus G at the splice site of about 40% clearly distinct from the 50% expected for I/I homozygotes (FIG. 1A). The $F_1$ progeny from these founders fell into two groups, 25% and 33% of A, whereas the $F_1$ progeny from I/I homozygotes were found in the 33% cluster only (FIG. 1B). The progeny group with 33% A was consistent with the genotype I/i whereas we postulate that animals in the 25% group have received a variant Dominant white allele with three copies of KIT and only one of the copies carries the splice mutation. The segregation data in this pedigree were consistent with this interpretation. There was no clear phenotypic difference between the two forms of the Dominant white allele. We suggest the designation $I^1$ for the allele with two KIT copies and one splice mutation and $I^2$ for the allele with three copies and one splice mutation.

The expected ratio of the splice mutation among the $F_2$ progeny could be predicted on the basis of the combination of our interpretation of the KIT genotype of the founder and $F_1$ animals, the coat color, and the segregation of closely linked microsatellites previously investigated. There was an excellent correlation between the predicted and observed ratio of the splice mutation obtained by the combined use of minisequencing and pyrosequencing (FIG. 1C).

The constitution of the observed KIT alleles and the corresponding genotypes are compiled in FIG. 2 and Table 1, respectively.

Table 1. The percentage of the splice variant at nucleotide 1 in intron 17 of the porcine KIT gene in different genotypes.

| Genotypes | % of splice$^a$ |
|---|---|
| i, $I^{Be}$, $I^P$ $^b$ | 0 |
| $I^2/I^P$ | 20 |
| $I^2$/i, $I^2/I^{Be}$, $I^1/I^P$ | 25 |
| $I^1$/i, $I^1/I^{Be}$, $I^2/I^2$ | 33 |
| $I^1/I^2$, $I^3/I^P$ | 40 |
| $I^1/I^1$, $I^3$/i, $I^3/I^{Be}$, $I^2/I^3$ | 50 |
| $I^1/I^3$ | 60 |
| $I^3/I^{3c}$ | 66 |

$^a$% splice = (number of copies with the splice variant/total gene copy number) × 100.
$^b$All possible genotype combinations of these alleles.
$^c$This genotype has not yet been observed.

The variability in gene copy number among KIT alleles is confirmed by quantitative real-time PCR analysis: In order to exclude the possibility that part of the observed variability in the ratio of the splice mutation is due to a biased PCR amplification (e.g. due to a polymorphism in a primer site), we tested our interpretation of the number of gene copies in different KIT alleles using real-time PCR analysis. The test was carried out by amplifying KIT and a single copy control sequence (the estrogen receptor gene, ESR). The copy number of KIT and ESR sequences in samples of genomic DNA correlates with the Ct values, which are estimates of the number of cycles needed to reach a given fluorescence threshold. The difference in Ct(ESR) and Ct(KIT) was plotted against the predicted number of KIT copies in different genotypes according to our interpretation of all animals in the Wild Boar intercross (FIG. 3). Although there was a large overlap between genotype classes, the Ct(ESR)-Ct(KIT)-difference showed a highly significant positive correlation to the predicted copy number (P<0.0001). The estimated means for the Ct difference for different genotype classes were as follows (means±SE): 2 copies, −0.57±0.17;

3 copies, −0.18±0.13; 4 copies, 0.36±0.17; 5 copies, 1.19±0.40. This result is in good agreement with the theoretical expectation of a ΔCt value of −1.0 when the copy number of a DNA sequence is doubled. The results confirm our interpretation of variation in copy number among KIT alleles and the existence of a KIT triplication. The large overlap in ΔCt values between genotype classes makes the TaqMan assay unsuitable for genotyping, at least with the experimental procedures used in this study.

Extensive allelic diversity in commercial white populations: Our observation of the presence of at least four different alleles ($I^1$, $I^2$, $I^{Be}$ and $I^P$) at the KIT locus among only eight Large White founder animals prompted us to investigate the allelic diversity in commercial white populations. Genomic DNA samples from 33 Swedish Large White pigs and 48 Swedish Landrace pigs were subjected to pyrosequencing and minisequencing analysis (FIG. 3). The results revealed a considerable allelic diversity in both populations, and that is likely to be a common feature in most white populations around the world. It is not possible to deduce exactly which alleles are segregating in these two populations without any pedigree data, but it is obvious that alleles without the splice mutation are segregating in both populations. Evidence for a sixth allele at the Dominant white/KIT locus was obtained since four Large White animals showed an approximately 60% ratio of the splice mutation, which is significantly higher than any of the genotype combinations formed by the alleles described above. Real-time PCR analysis using KIT and ESR indicated that these four animals carried five copies of KIT. We therefore postulate that they are heterozygous for a KIT-allele with three gene copies of which two carry the splice mutation. We have designated this allele $I^3$ (FIG. 2; Table 1). Two of the four animals carrying the $I^3$ allele were half-sibs and all four shared a common grandsire suggesting that they had inherited $I^3$ from this common ancestor.

If we assume that most of the animals in the 50% cluster are homozygous $I^1/I^1$ we can obtain a rough estimate of the frequency of this allele by the square root of the frequency of this genotype class. This gives allele frequency estimates of 0.49 and 0.58 for $I^1$ in these Large White and Landrace populations, respectively. These are most likely slight overestimates since other genotype classes also give a 50% ratio (Table 1).

Discussion

The extensive genetic diversity at the pig Dominant white/KIT locus detected in this study was unexpected considering the strong selection for white color for more than 100 years. It was also unexpected from the literature on pig coat color genetics in which it is assumed that white breeds are homozygous I/I (e.g. Legault 1998). The present study clearly indicates that this locus is genetically unstable. The reason for this is most likely that the duplication is large (about 400 kb) and that the two copies show a very high sequence identity (>99%) facilitating the generation of new alleles by unequal crossing-over and possibly by gene conversion. This is a very well documented phenomenon for tandemly duplicated DNA fragments (Ohta et al. 1990). For instance, unequal crossing-over between the tandem copies of the genes for red/green eye pigment genes on the human X-chromosome has generated haplotypes associated with color blindness (Neitz and Neitz 1995).

We have now documented at least six different Dominant white/KIT alleles. It is an open question whether the alleles associated with the Belt phenotype in Hampshire pigs and the Roan phenotype in our Wild Boar intercross are identical. Both alleles contain a single KIT copy without the splice mutation. We have designated the allele associated with these two phenotypes $I^{Be}$ to be conservative and not introduce a new allele designation without compelling evidence for the allele being distinct from previously described alleles. The reason for our caution is that the phenotypic expressions of KIT alleles show interaction with other genes, in particular the MC1R/Extension locus (Marklund et al. 1998; Giuffra et al. 1999; this study). We have so far not observed the Belt-associated allele and the Roan-associated allele on the same genetic background.

It is possible that the presence of multiple KIT alleles in white pig breeds is simply explained by a high mutation rate. However, balancing selection may contribute to the maintenance of allelic diversity. It is well documented in the mouse that structural KIT mutations are associated with pleiotropic effects on hematopoiesis and fertility and loss-of-function homozygotes are lethal (Jackson 1994). It is very likely that the splice mutation present in I alleles is a complete loss-of-function as regards KIT signaling since certain missense mutations in the corresponding region in mouse are non-functional and homozygous lethal. We have reported that I/I homozygotes had a lower number of white cells than I/i and i/i animals in our Wild boar intercross, suggesting that the I allele is associated with mild negative effects on hematopoiesis (Marklund et al. 1998). It will therefore be of considerable interest to investigate hematopoietic parameters and possibly fertility traits among different KIT genotypes, in particular the phenotypic effect in $I^3/I^3$ homozygotes in which 66% of the expressed KIT protein is expected to possess the splice form lacking 41 amino acids of the tyrosine kinase domain. It is also possible that an allele containing a single KIT copy and the splice mutation occurs at a low frequency in some white populations and this allele is expected to be homozygous lethal.

The results of this study have important implications for practical pig breeding. Firstly, both the pyrosequencing and minisequencing methods applied in this study are major improvements with regard to KIT genotyping. Neither the TaqMan method nor quantification of PCR-RFLP fragments that have previously been used for quantitative analysis of KIT alleles are able to resolve the allelic diversity to the same extent as reported here. For instance, the diagnostic test can be used to ensure that white boars are homozygous I/I and thus breed true for white color also in crosses with colored lines; in many markets there is a strong consumer preference for pig meat with white skin. Secondly, the present study implies that the genetic instability at the KIT locus causes a cost in pig breeding as a part of the selection potential is devoted to maintaining the white color. The economic consequences are probably small in each generation but could be substantial when summed over many generations. Finally, it is worthwhile to investigate whether some Dominant white/KIT alleles are associated with negative pleiotropic effects on other traits. If so, a diagnostic DNA test should be used to ensure that the frequency of such deleterious alleles is kept low.

Another interesting implication of the instability of the Dominant white/KIT locus is that white domestic pigs that are able to establish wild feral pigs are expected to revert to the wild-type genotype at the KIT locus and to a colored phenotype. This is because the white color will have negative effects on the fitness in the wild both because of a higher susceptibility to sun exposure and a higher susceptibility to predation and human hunting.

EXAMPLE 2

Pulsed Field Gel Electrophoresis (PFGE) and Southern blot analysis. DNA plugs were prepared from fresh or frozen blood of Duroc (i/i), Hampshire ($I^{Be}/I^{Be}$), and Large White (I/I) pigs. White cells were prepared by isotonic lysis, washed two-three times in phosphate-buffered saline, resuspended to obtain a concentration of 25×10$^6$ cells/ml and mixed with an equal volume of 1.5% low-melting agarose in phosphate-buffered saline cooled to about 50° C. Aliquots of the agarose-cell suspension were placed in plug molds (BiORad) and allowed to solidify at 4° C. Plugs were digested for 1-2 days at 50° C. with constant shaking in 0.5 M EDTA, pH 8.0, 1% Sarkosyl, 0.5 mg/ml Proteinase K. After equilibration in TE, plugs were incubated in TE containing 1 mM phenylmethylsulfonyl fluoride to inactivate residual Proteinase K activity. After extensive washing in TE, the plugs were stored at 4° C. in 0.5M EDTA or directly used for restriction digestion. Each plug was divided in two parts of approximately 35 µl and equilibrated for about 3-4 hr on ice in the restriction buffer provided by the manufacturer (New England Biolabs, USA). The buffer was replaced by fresh buffer containing about 50 U of enzyme and the enzyme was allowed to diffuse into the plug for 16 hours at 16° C. After incubation at 37° C. for 16 hr, about 20 units of enzyme were added, allowed to diffuse into the plug for 4-5 hr at 16° C. and incubated at 37° C. for an additional 5-6 hr.

PFGE of the digested plugs was performed in a CHEF Mapper XA apparatus (BiORad, USA) at 14° C. in a 1% agarose gel in 0.5×TBE. Electrophoresis conditions were set by the Auto Algorithm Mode to obtain the optimal resolution for the expected fragment sizes, typically between 50 kb-800 kb (pulse times of 6 s to 1.3 min, in an electric field of 6 V/cm for 27 hr). Yeast chromosomes and Lambda ladder (BiORad, USA) were used as size markers. DNA separated by PFGE was transferred for 3 hr to a Hybond N+ (Amersham, UK) membrane by standard conditions for Southern Blotting.

Blot hybridizations were performed in ExpressHyb Hybridization Solution (Clontech, USA) in the conditions recommended by the manufacturer. The DNA probes used were: a 2.4 kb BamH I/Sal I fragment of the pig KIT cDNA (Marklund et al. 1998), a 3.4 kb BamH I fragment of the human PDGFRA cDNA (Claesson-Welsh et al. 1989), a 4.5 kb XhoI/XbaI fragment of human KDR cDNA (GenBank AF063658), a 229 bp KIT intron 18 PCR fragment (Johansson Moller et al. 1996), and four STS probes obtained from end-sequencing of the BAC clones of the contig: STS 1000D25', STS 211E125', STS 645D53', and STS 953F113'. Probes were labeled with $^{32}$P-dCTP using the Megaprime DNA Labelling System (Amersham, UK). Hybridized blots were exposed in a PhosphorImager (Molecular Dynamics, USA) for at least 16 hr.

Southern blot analysis of HindIII digested BAC DNA and genomic DNA was carried out as previously described (Johansson Moller et al. 1996). A 897 bp PCR product from the 3.9 kb subclone p953Hind4 containing the 3'-5' duplication breakpoint was used as probe.

Construction of BAC contig. The INRA porcine BAC library was constructed using the pBeloBAC11 vector (Rogel-Gaillard et al. 1999). BAC clones were isolated by three-dimensional PCR-based screening. PCR was done in a 20 µl reaction volume containing 0.2 mM of each dNTP, 1.5 mM MgCl$_2$, 8 pmoles of each primer, 2 U Taq DNA polymerase and reaction buffer (Advanced Biotech, UK).

The cycling conditions included an initial incubation at 94° C. for 5 min followed by 3 cycles comprising 1 min at 94° C., 1 min at the optimal annealing temperature for a given primer set plus 2° C. and 1 min at 72° C., and 35 cycles of 20 s at 94° C., 30 s at the optimal annealing temperature and 30 s at 72° C.

BAC end sequences were determined by direct sequencing of both the 5' and 3' ends of selected BACs using the M13R and M13F primers. Briefly, BAC DNA from 100 ml liquid culture (LB+12.5 µg/ml chloramphenicol) was prepared by an alkaline lysis method. Crude BAC DNA was digested with 40 units of EcORV. Digested DNA was purified with the QIAEX II kit (QIAGEN, Germany) according to the company's instruction, followed by ethanol precipitation and used in 10 µl sequencing reactions with BigDye Terminator chemistry (PE Applied Biosystems, USA). Forty-five cycles composed of 95° C. for 5 s, 50° C. for 10 s and 60° C. for 4 min were applied and extended products were ethanol precipitated, loaded on a 4% denaturating gel and separated on an ABI377 sequencer (PE Applied Biosystems, USA). Approximately 400-500 bp good sequence was usually obtained. The sequences were masked for interspersed repeats and low complexity pig DNA sequences using RepeatMasker. Masked sequences were subjected to BLAST (Altschul et al. 1990) searches against DNA databases (nr, month, and dbest) at NCBI using the advanced BLAST version 2.0 network service. The BAC end sequences defined new Sequence Tagged Sites (STSs) that were used to screen the library again and expand the contig. The order and overlap of the BAC clones were determined by screening the STSs against all clones in the contig.

The overlap and physical distances between BAC clones were estimated by restriction mapping. The rare cutting enzymes SmaI and NotI (Amersham, UK) were used for complete and partial digestions. Fragments were separated by PFGE as described above and transferred to Hybond N+ hybridization membranes (Amersham, UK). The vector specific primers SP6 and T7 were endlabeled with $^{32}$p using T4 Polynucleotide Kinase (New England Biolabs, UK) and used for hybridization.

FISH analysis. This was carried out as previously described in detail (Chowdhary et al. 1995). BACs were labelled with biotin-14-dATP using the GIBCO BRL Bionick labelling system (BRL 18247-015) and approximately 200 ng of the probe were added to each chromosome slide. A cosmid clone containing part of the KIT coding sequence (Johansson Moller et al. 1996) was labelled with digoxigenin-11-dUTP by nick translation and cohybridized with each of the new BAC clones. The biotin signal was detected with two layers of fluorescein isothiocyanate (FITC)-conjugated avidin (Vector) and the digoxenin signal was detected with anti-dig Rhodamine (Boehringer-Mannheim). The chromosomes were counterstained with DAPI (4',6-diamino-2-phenylindole) to produce a G-band like pattern for chromosome identification.

Subcloning and sequence analysis of the duplication breakpoints. PCR amplification of the duplication breakpoints. Fragments spanning the breakpoints were amplified from pig genomic DNA samples representing the Wild Boar, Large White, Landrace, Pietrain, Berkshire, Duroc, Hampshire, Linderöd, and Meishan breeds. The primers 832F2 (5'-CCA CAA TAT ACC TAC CAG AAT TAC-3') (SEQ ID NO: 5) and 953R2 (5'-AAG GTG TGG ATC AAA TCT GGT C-3') (SEQ ID NO: 6) were used to amplify 968 bp spanning the 5' breakpoint present in BAC832E11; 953F1 (5'-GTT CAA TCC AGC AAT CAC AAC C-3') (SEQ ID NO: 7) and 953R2 were used to amplify 864 bp spanning the 3'-5' breakpoint present in BAC953F11; and 953F1 and 1041R1 (5'-TTT TAA TCC TCT TAA GGA CCA AC-3') (SEQ ID NO: 10) were used to amplify 1022 bp spanning the 3' breakpoint present in BAC 1041B3. The PCR reactions were performed in 10 µl reactions including 1.5 mM $MgCl_2$, 0.2 mM of each dNTP, 2.5 pmol of each primer, 5% DMS0, 25 ng genomic DNA. 1x PCR GOLD buffer, and 0.75 U AmpliTaq GOLD polymerase (PE Applied Biosystems, Foster City, CA, USA). Thermocycling was carried out using a PTC 200 instrument (MJ Research, Watertown, MA, USA). The temperature conditions in the first cycle were 94° C. for 10 min, 55° C. for 30 s, and 72° C. for 90 s whereas the remaining cycles were performed at 94° C. for 30, 52° C. for 30 s, and 72° C. for 90 s. The PCR products were directly sequenced as described above.

The primers 953F9 (5'-TAA GTG AAA GAA GTC AAT CTG AG-3') (SEQ ID NO: 11) and 953R3 (5'-GGC AGT CAT GTA ACT ATC ACC-3') (SEQ ID NO: 12) were used to generate a 152 bp product spanning the 3'-5' breakpoint as a diagnostic test for the duplication. The product was separated by standard agarose gel electrophoresis.

Results

Pulsed Field Gel Electrophoresis (PFGE).

DNA samples from pigs representing three breeds, Duroc, Hampshire, and Large White, and the three Dominant White/KIT genotypes i/i, $I^{Be}/I^{Be}$, and I/I, respectively, were used. DNA plugs containing high-molecular weight genomic DNA were digested with three rare-cutting enzymes NarI, BssHII, and PmeI.

The digested DNA were separated by PFGE and blotted to hybridization membranes. The membranes were first hybridized with KIT probes and cDNA probes for the PDGFRA and KDR genes, which are located upstream and downstream of KIT, respectively, in the human genome (Spritz et al. 1994). The results showed as expected that KIT hybridized to the duplicated region since 2-3 fragments were obtained for both NarI and BssHII in Large White pigs but only a single fragments in non-white pigs (Table 1; FIG. 1A). The PDGFRA probe hybridized to a single fragment with all enzymes and in all genotypes indicating that the duplication does not involve this gene in agreement with our previous FISH analysis (Johansson Moller et al. 1996). Similarly, the KDR probe hybridized to a single fragment in Large White pigs with all three enzymes.

Figure 5B:
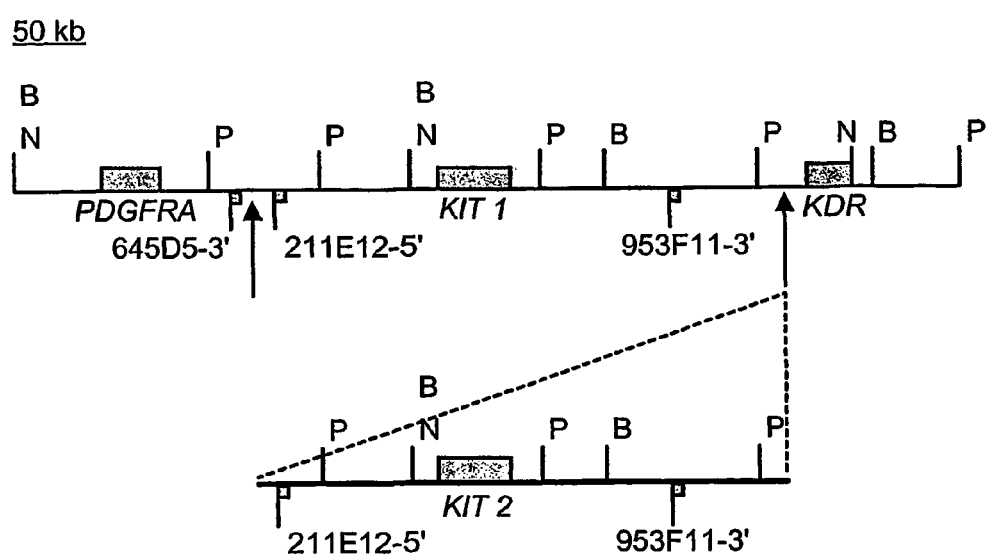

The results indicated that one duplication breakpoint is located between PDGFRA and KIT while another is located between KIT and KDR (FIG. 1B). In order to refine the location of the former duplication breakpoint we used two STS fragments 645D53' and 211E125' from the region between KIT and PDGFRA. The probes were hybridized to the PFGE blots and the results showed that the duplication breakpoint is located between these two STSs (Table 1; FIG. 5B).

The PFGE data suggested that there was a single NarI fragment within the duplicated region and consequently that the size of the duplication is approximately 600 kb.

Construction of a BAC Contig.

The BAC library was constructed from a Large White pig assumed to be homozygous I/I. We have arbitrarily designated the normal gene copy KI2 and the copy containing the splice mutation KI3. The construction of the BAC contig was initiated by screening the library with primers amplifying MIT exons. We were able to assign these BAC clones as belonging to KI2 or KI3 using the diagnostic test for the splice mutation (FIG. 6); it should be noted that we do not know in which order the two copies are organized in relation to PDGFRA and KDR. The contig was expanded on both sides by chromosome walking using STSs developed by BAC end sequencing. The clone 211E12 contains KIT exon 1 and parts of the upstream region while clone 549C3 represents the KIT downstream region. We were not able to assign these clones to the KI2 or KI3 region since no diagnostic polymorphism between these regions has yet been detected.

The closely linked PDGFRA gene was chosen as a second starting point for building the BAC contig. PCR primers were designed using PDGFRA sequences conserved between human and mouse (Table 2). Two positive clones were identified (FIG. 6). The BAC ends were sequenced and used to develop new STS primers which in turn was used to expand the contig on both sides of PDGFRA. Six additional clones were identified and subjected to BAC end sequencing. BLAST searches using the STS 642D43' revealed a highly significant homology to the human PDGFRA promoter region. This result provided an orientation of this subcontig and the chromosome walking was continued from the PDGFRA 3'-end with the assumption that PDGFRA and KIT are oriented head-to-tail in pigs as in humans (Spritz et al. 1994). The screening of the BAC library with STS 645D53' identified two new clones and one of these 832E11 overlapped with clone 211E12 showing that a complete contig between PDGFRA and KIT had been constructed (FIG. 6). The distance between the two genes in the pig was estimated to about 350 kb very similar to the corresponding estimate for the mouse (Hough et al. 1998).

The PFGE data indicated that the KIT 5' duplication breakpoint should be located between STS 645D53', which did not hybridize to a duplicated fragment, and 211E125', which hybridized to two copies of the KIT region (FIG. 5). These two STSs are about 100 kb apart and both present in BAC 832E11 which should thus contain the 5' duplication breakpoint. The BAC library was then screened with STS 211E125' with the assumption that this STS should be able to identify BACs from the 5' duplication break-point as well as from the 3'-5' duplication breakpoint (see FIG. 6). The characteristic feature of the latter types of clones would be that they should contain one end not belonging to the PDGFRA-KIT contig. Three new clones were isolated using STS 211E125' and new STSs were generated by BAC end sequencing. PCR screening of the BACs from the contig revealed that both 763F13' and 953F113' were only positive with themselves, indicating that the corresponding clones potentially represented the 3'-5' duplication breakpoint. FISH analysis of 763F1 and five new BAC clones isolated with 763F13' showed that this clone was chimaeric with one end from the KIT region on chromosome 8 and the other end originating from chromosome 5. However, FISH analysis of clone 953F11 only resulted in a signal from the KUT region on SSC8q12. STS 953F113' was then used to isolate four new BACs (FIG. 2). BAC end sequencing and BLAST searches against GenBank revealed a highly significant hit between the 3'-end of clone 1041B3 and the KDR coding sequence in different species; the highest score was obtained against human KDR, AF063658 (94% sequence identity over 93 nucleotides, $P=1e^{-32}$). This together with the PFGE data showing that KDR is not duplicated provided evidence that clone 953F11 contains the 3'-5' duplication breakpoint and that clone 1041B3 contains the 3' duplication breakpoint. PCR screening using the STSs isolated from BAC 549C3 from the 3'-region of KIT revealed that the 5' STS was positive with 391B8 and 568E1 indicating that the contig from KIT to KDR had been closed. This allowed us to estimate the distance between KIT and KDR to about 250 kb and the size of the entire KIT duplication to about 450 kb (FIG. 6).

Identification and Characterization of the Duplication Breakpoint.

A Southern blot of HindIII digested DNA from the three BAC clones 832E11, 953F11, and 1041B3 containing the three duplication breakpoints was hybridized with radioactively labeled BAC DNA from 953F11; HindIII was chosen for this instrument since partial HindIII digestions were used for the construction of the BAC library. FIG. 3A shows that BAC 953F11 contained a 3.9 kb HindIII fragment that was unique to this clone whereas all other fragments were also present in 832E11, 1041B3, or both (fragments representing the BAC vector). The results confirm that BAC953F11 represents the 3'-5' duplication breakpoint and that this appears to be a recent duplication since no HindIII restriction site have been gained or lost, and no large insertions/deletions have occurred since the duplication event.

The 3.9 kb HindM fragment from 953F11 was subcloned into pUC18 to generate clone pUC953H4. The fragment was sequenced using vector primers and primer walking. The corresponding sequence from BAC 832E11 and 1041B3 was generated by PCR amplification and direct sequencing. The sequence comparison revealed that 953F11 was a hybrid between the sequences of 832E11 and 1041B3 as expected. Bioinformatic analysis using Repeatmasker (ref) showed that the 3.9 kb fragment contained several repetitive elements and that the actual duplication breakpoint occurred within a hybrid LINE element partly corresponding to a LINE element in 832E11 and partly to a LINE element in 1041B3 (FIG. 8). BLAST analysis showed that a region about 1 kb 3' of the duplication breakpoint and also present in 832E11 showed several highly significant hits to the human draft genome sequence from the region between PDGFRA and KIT (ref). The human region is located about 150 kb upstream of KIT exon 1 in good agreement with the location of the corresponding region in pig (FIG. 6).

A sequence comparison of 1195 bp of 953F11 and the corresponding region in 1041B3 revealed no sequence difference and a comparison between about 2450 kb of 953F11 and the corresponding region in 832E11 revealed two differences, one extra nucleotide at a mononucleotide repeat and a single base substitution (data not shown). The results indicate that the KIT duplication occurred recently or that the sequences are homogenized by gene conversion.

Distribution of the KIT Duplication Among Pig Breeds.

Southern blot analysis of HindIII genomic DNA was used to confirm that BAC953F11 represented the true duplication breakpoint and was not a cloning artifact. A PCR fragment free of known repetitive sequences from subclone pUC953H4 was used as probe. The results showed that the 4.5 kb fragment was present in Large White and Landrace animals carrying various Dominant white alleles but not in the Wild boar (FIG. 7B). Interestingly, a considerable variation in the hybridization signal of the 3.9 kb fragment was observed and the results were consistent with our recent analysis of a variation in KIT copy number in white breeds (Pielberg et al. submitted). Large White female W5 (lane 3) is heterozygous for a duplication and a triplication (five KIT copies in total), W6 (lane 4) is heterozygous for the duplication (three copies), whereas W7 and 8 (lanes 5 and 6) are homozygous for the duplication (four copies) (FIG. 7B).

PCR screening showed that the KIT duplication was present in Large White and Landrace animals but not in Wild boar, Berkshire, Duroc, Hampshire, Linderöd or Meishan pigs as expected (Table 2). Unexpectedly, four out of five Pietrain pigs were positive for the KIT duplication despite the fact that this white pig with black spots are assumed to be homozygous i/i. Interestingly, the single Pietrain pig which did not carry the duplication was sent to us since it was atypical for the breed and almost entirely black. Its parents had the usual color and both carried the KIT duplication. A PCR test for the splice mutation (Marklund et al. 1998) showed that all Pietrain pigs were negative which indicates that they carry the $I^P$ allele.

TABLE 1

Restriction fragment sizes observed in PFGE analysis of the PDGFRA-KIT-KDR region on pig chromosome 8.

| Restriction enzyme | Breed | PDGFRA cDNA | STS 645D53' | STS 211E125' | KIT intron 18 (and cDNA) | STS 952F113' | KDR cDNA |
|---|---|---|---|---|---|---|---|
| NarII | D | 450 | 450 | 450 | 450 | — | 450 |
|  | H | 450 | 450 | 450 | 480 | — | 480 |
|  | LW | 450 | 450 | 450, 590, 620 | 480, 590, 620 | — | 480 |
| BssHII | D | 450 | 450 | 450 | 200 | 320 | 320 |
|  | H | 450 | 450 | 450 | 225 | 320 | 320 |
|  | LW | 450 | 450 | 450, 400 | 210, 215, 225 | 320, 400 | 320 |
| PmeI | D | — | 130 | 130 | 410 | 410 | 225 |
|  | H | — | 130 | 130 | 240 | 240 | 225 |
|  | LW | — | 130 | 130, 100 | 240 | 240 | 225 |

D = Duroc; H = Hampshire; LW = Large White; "—" = not tested

TABLE 2

Presence of the unique duplication breakpoint in the KIT region associated with Dominant white colour in different breeds of pigs

| Breed/ population | Coat colour | Presumed genotype | Presence of duplication + | Presence of duplication − | Total |
|---|---|---|---|---|---|
| Wild Boar | wild type | i/i | 0 | 2 | 0 |
| Large White | white | I?I? | 11 | 0 | 11 |
| Landrace | white | I?I? | 4 | 0 | 4 |
| Pietrain | white/black spots | i/i | 4 | 1 | 5 |
| Berkshire | black/white points | i/i | 0 | 4 | 4 |
| Duroc | red | i/i | 0 | 4 | 4 |
| Hampshire | black/white belt | $I^{Be}I^{Be}$ | 0 | 4 | 4 |
| Linderod | red/black spots | i/i | 0 | 1 | 1 |
| Meishan | black | i/i | 0 | 3 | 3 |

I? indicate that the allele may be $I^1$, $I^2$, $I^3$ or $I^P$

EXAMPLE 3

A sample of 375 sows with reproduction records were genotyped for the KIT splice variant.

All sows farrowed at the same farm, 954 of the litters were from matings with sires from the same line, the other 149 litters were from crossbreed matings.

Three traits were analysed, total numbers born (TNB), numbers born alive (NBA) and numbers stillborn (NBD).

Data were analysed using the PROC MIXED procedure of SAS. Fixed effects included in the model were: year-month of farrowing, cycle (1, 2, 3+) and number of services (1, 2). Sire of the sows was included as a random effect with $h^2=0.10$. KIT genotype was included as a fixed effect. The interaction between litter cross type or cycle with KIT genotype or phenotypic colour was tested but was not significant.

The results show a tendency for the ii (KIT wild type) to have a lower TNB and also lower number of stillborn piglets. In situations where the number of embryos in utero is very high, sows with the ii genotype may have an advantage over those carrying the splice mutation. Furthermore, as it is likely that the splice mutation is a complete loss-of-function mutation as regards KIT signalling, it is anticipated that the $I^3$ allele containing two copies of the splice mutation may be associated with a lower litter size than the alleles containing 1 ($I^1$ and $I^2$) or zero copies of the splice mutation (I, $I^{Be}$ or F).

| Marker Genotype | | TNB | NBA | NBD |
|---|---|---|---|---|
| KIT genotype | ii (Splice absent) | 12.73 (0.35) | 12.56 (0.35) | 0.17 (0.35) |
| | Ii/Ii (Splice present) | 13.00 (0.23) | 12.53 (0.23) | 0.47 (0.23) |
| | Sig. | P > 0.3 | P > 0.9 | P > 0.3 |

EXAMPLE 4

A sample set from a Large White population was identified which had high or low litter size based on Breeding Value (BV) for total numbers born (using the PEST program). The top 50 and bottom 50 sows per group, with DNA samples, were identified and DNA was sent for KIT typing. Additional samples were also genotyped to estimate the distribution of splice ratios in this population.

The splice ratios obtained were grouped as shown in FIG. 12. This figure also shows the distribution of splice ratios in this group of animals.

Least squares means for splice ratio were estimated for animals in the top (T) or bottom (B) litter size groups. There was no significant difference in splice ratio between high or low litter size groups (Table 3).

TABLE 3

LSMeans for splice ratio by litter size group (Bottom or Top)

| | BV | |
|---|---|---|
| Group | Mean | S.E. |
| B | 0.526 | 0.016 |
| T | 0.506 | 0.016 |
| Prob. | P > 0.40 | |

Least squares means were estimated for the litter size traits per splice ratio group (1, 25, 40, 50, 60). There was a significant difference in BV between splice groups (P<0.01, FIG. 13).

Frequencies between splice ratio groups within the BV litter size trait were compared to test whether there was any distortion in the frequencies. Results indicated frequency distortions for the 0, 40 and 50 groups where there was an over-representation of the 25 and 50 splice groups in the B sows and an over-representation of the 40 splice group in the T group.

TABLE 4

Frequency of splice groups in B or T sows per litter size trait.

| Trait | Splice group | Numbers B | Numbers T | Proportions $P_b$ | Proportions $P_t$ | Average ($P_a$) | z | Sig. level |
|---|---|---|---|---|---|---|---|---|
| BV12 | 0 | 0 | 2 | 0.00 | 0.04 | 0.02 | 1.43 | P < 0.20 |
| | 25 | 9 | 5 | 0.18 | 0.10 | 0.14 | 1.15 | n.s. |
| | 40 | 3 | 12 | 0.06 | 0.24 | 0.15 | 2.52 | P < 0.05 |
| | 50 | 38 | 30 | 0.76 | 0.60 | 0.68 | 1.71 | P < 0.10 |
| | 60 | 0 | 1 | 0.00 | 0.02 | 0.01 | 1.01 | n.s. |

$$z = \frac{P_t - P_b}{\sqrt{Pa(1-Pa)(1/Nt + 1/Nb)}}$$

Conclusions

A distortion in the frequency of splice groups between high and low litter size animals was detected for the trait BV.

The apparent lower BV genotype classes are those with 25% (although not significant) and 50% KIT ratios. In this population, these ratios correspond to genotypes that include at least one copy of the dominant white allele (I), although there are other possibilities for this ratio and it is likely to be population specific. In this case the most likely combinations are I with $I^P$ (25%) and homozygous for 1 (50%). The 40% class is apparently preferred, however, it is also expected that this genotype class will contain the dominant white allele (1), although in this case it will be with a copy of the triplicated gene with a single splice site. This suggests that there may be a negative effect of the splice variant on litter size although the mechanism is not clear. The significant effects were seen for two copies of I (50%, 2 two splice variants and two "normal" copies of KIT) and 40% where there are 2 copies of the splice variant and 3 copies of the "normal" KIT gene. It is hypothesized that a negative impact on litter size would lead to accumulation of alleles with a reduction in the splice variant.

EXAMPLE 5

Samples were collected from eight different white dam lines consisting on Large White, Landrace and synthetic lines (or populations).

The ratio of the KIT splice variant and the "normal" KIT gene were determined using the Pyrosequencing method.

This ratio was then converted to the most probable alleles by simple analysis of the frequencies and the most probable fit. The results are shown in Table 6 and FIG. 14.

TABLE 5

| Line | KIT allele frequency | | | | number |
|---|---|---|---|---|---|
| | I | $I^P$ | $I^2$ | $I^3$ | |
| A (Large White) | 0.60 | nd | 0.40 | nd | 20 |
| B (Large White) | 0.85 | 0.13 | 0.02 | nd | 20 |
| C (Large White) | 0.47 | 0.13 | 0.40 | nd | 20 |
| D (Large White) | 0.74 | nd | 0.26 | nd | 19 |
| E (Large White synthetic) | 0.35 | 0.05 | 0.60 | nd | 20 |
| F (Landrace) | 0.55 | 0.15 | 0.28 | 0.02 | 20 |
| G (Landrace) | 0.47 | 0.16 | 0.37 | nd | 19 |
| H (Landrace synthetic) | 0.52 | 0.11 | 0.37 | nd | 19 |

The estimates are conservative and they do not take into account the possibility of rare alleles. Allele $I^3$ was identified in line F as a large splice ratio was identified for some samples in this line, which would correspond to an animal with the genotype $I/I^3$.

However, despite this limitation the results confirm that there is significant variation in KIT allele frequency in different white lines of pigs, with $I^2$ and $I^P$ being identified in most lines as well as the dominant white I allele.

In general there is a low or moderate frequency of the $I^P$ allele (associated with colour when this allele is combined with the wild type i allele, [e.g. in a mating between an animal carrying an $I^P$ allele and a coloured breed or a heterozygote Ii animal] with the degree of colour of the offspring in part being determined by the allele at the unlinked extension locus). However, this allele was not detected in two of the Large White lines (lines A and D).

The triplicated allele with one copy of the splice mutation was at a relatively moderate or high frequency in all but one of the lines (line B). This allele has been hypothesised to moderate a negative effect of the dominant allele I on litter size, which may explain its high frequency in these dam lines selected for litter size.

The triplicated allele with two copies of the splice mutation was found very rarely, with only line F showing this allele. Although the assignment of alleles is based on a conservative system that assumes the frequency of this allele is very low (see above).

It is envisaged that the Ip allele would be selected against to ensure that progeny from these lines crossed with coloured breeds would be guaranteed to be white irrespective of the genotype of the coloured breed. Selection decisions could also be taken on the $I^2$ and $I^3$ alleles based on association with performance (or colour).

EXAMPLE 6

Sows from a synthetic line segregating for dominant white (I) and "wild type" alleles with litter size records were analysed for their KIT genotype. In this case a distinction was only made between I and i. Animals were compared that had either 0, 1 or 2 copies of the marker allele associated with "i".

Results were as shown in Table 6.

TABLE 6

| | number of "i" associated alleles: | | | |
|---|---|---|---|---|
| | 0 | 1 | 2 | |
| Number of Sow | 268 | 191 | 14 | |
| Number of litters | 1452 | 1037 | 80 | |
| LSmean of Total Number Born: | 11.35 | 11.59 | — | p < .05 |
| LSmean of Number born alive: | 11.61 | 11.81 | — | p < .10 |
| Litter weight at birth: | 11.84 | 11.53 | — | p < .001 |

"—" in the 4th column (under 2 copies of "i") means the numbers in this class were too small to estimate a LSmean value.
The p-values are, for testing a difference between the "0" and "1" class.

The results suggest that there is a negative effect on LS of the I allele with the litters from sows homozygote for 1 (dominant white) having approximately 0.2 pigs less piglets per litter than animals with only one copy of the I allele.

This suggests that the splice variant that is present in the dominant white allele may have a negative impact on litter size. It may therefore be advantageous, where litter size is an important trait to control the frequency of I and the other allelic forms such as $I^3$ depending on the need to maintain white coat colour in the line.

References

CHABOT, B., D. A. STEPHENSSON, V. M. CHAPMAN, P. BESMER and A. BERSTEIN, 1988 The proto-oncogene c-kit encoding a transmembrane tyrosine kinase receptor maps to the mouse Wlocus. Nature 335: 88-89.
FLEISCHMAN, R. A., D. L. SALTMAN, V. STASTNY and S. ZNEIMER, 1991 Deletion of the c-kit protooncogene in the human developmental defect piebald trait. Proc. Natl. Acad. Sci. 88: 10885-10889.

GEISSLER, E. N., M. A. RYAN and D. E. HOUSMAN, 1988 The dominant white spotting (W) locus of the mouse encodes the c-kit proto-oncogene. Cell 55: 85-192.

GIEBEL, L. B. and R. SPRITZ, 1991 Mutation of the KIT (mast/stem cell growth factor receptor) protooncogene in human piebaldism. Proc. Natl. Acad. Sci. 88: 8696-8699.

GIUFFRA, E., G. EVANS, A. TÖRNSTEN, R. WALES, A. DAY, et al., 1999 The Belt mutation in pigs is an allele at the Dominant white (I/KIT) locus. Mamm. Genome 10: 1132-1136.

HUBBARD, S. R., L. WEI, L. ELLIS and W. A. HENDRICKSON, 1994 Crystal structure of the tyrosine kinase domain of the human insulin receptor. Nature 372: 746-754.

JACKSON, I. J., 1994 Molecular and developmental genetics of mouse coat color. Annu. Rev. Genet. 28: 189-217.

JOHANSSON, M., H. ELLEGREN, L. MARKLUND, U. GUSTAVSSON, E. RINGMAR-CEDERBERG, et al., 1992 The gene for dominant white color in the pig is closely linked to ALB and PDGFRA on chromosome 8. Genomics 14: 965-969.

JOHANSSON MOLLER, M., R. CHAUDHARY, B. HELLMTN, B. HOYHEIM, B. CHOWDHARY, et al., 1996 Pigs with the dominant white coat color phenotype carry a duplication of the KIT gene encoding the mast/stem cell growth factor receptor. Mamm. Genome 7: 822-830.

KIJAS J. M. H., R. WALES, A. TÖRNSTEN, P. CHARDON, M. MOLLER, et al., 1998 Melanocortin receptor 1 (MC1R) mutations and coat color in pigs. Genetics 150: 1177-1185.

LAAN M., K GRÖN-VIRTA, A. SALO, P. AULA, L. PELTONEN, et al., 1995
Solid-phase minisequencing confirmed by FISH analysis in determination of gene copy number. Hum. Genet. 96: 275-280.

LEGAULT C., 1998 Genetics of colour variation. In *The Genetics of the Pig*, M. F. ROTHSCHILD, A. RUVINSKY, eds (CAB International).

MARIANI, P., M. J. MOLLER, B. HOYHEIM, L. MARKLUND, W. DAVIES, et al., 1996 The extension coat colour locus and the loci for blood group O and tyrosine aminotransferase are on pig chromosome 6. J. Hered. 87: 272-276.

MARKLUND, S., J. KIJAS, H. RODRIGUEZ-MARTINEZ, L. RÖNNSTRAND, K. FUNA, et al., 1998 Molecular basis for the dominant white phenotype in the domestic pig. Genome Res. 8: 826-833.

NEITZ, M. and J. NEITZ, 1995 Numbers and ratios of visual pigment genes for normal red-green color vision. Science 267: 1013-1016.

OHTA T., 1990 How gene families evolve. Theor. Popul. Biol. 37: 213-219.

OLSSON C., E. WALDENSTRÖM, K. WESTERMARK, U. LANDEGREN, A.-C. SYVÄNEN, 2000 Rapid determination of the frequencies of ten alleles in Wilson's disease gene (ATP7B), in pooled DNA samples. Eur. J. Hum. Genet. 8: 933-938.

RONAGHI, M., M. UHLEN and P. NYREN, 1998 A sequencing method based on real-time pyrophosphate. Science 281: 363-365.

SYVÄNEN A.-C., A. SAJANTILA and M. LUKKA, 1993 Identification of individuals by analysis of biallelic DNA markers using PCR and solid-phase minisequencing. Am. J. Hum. Genet. 52: 46-59.

WISEMAN, J., 1986 *A history of the British pig*. Ebenezer Baylis & Son Ltd., Worcester, UK.

Altschul, S. F., W. Gish, W. Miller, E. W. Myers and D. J. Lipman, 1990 Basic local alignment search tool. J Mol Biol 215: 403-410.

Berrozpe, G., I. Timokhina, S. Yukl, Y. Tajima, M. Ono et al., 1999 The $W^{sh}$, $W^{57}$, and Ph Kit expression mutations define tissue-specific control elements located between −23 and −154 kb upstream of Kit. Blood 94: 2658-2666.

Chowdhary, B. P., C. de la Sena, I. Harbitz, L. Eriksson and I. Gustavsson, 1995 FISH on metaphase and interphase chromosomes demonstrates the physical order of the genes for GPI, CRC, and LIPE in pigs. Cytogenet. Cell Genet. 71: 175-178.

Claesson-Welsh, L., A. Eriksson, B. Westermark and C. H. Heldin, 1989 cDNA cloning and expression of the human A-type platelet-derived growth factor (PDGF) receptor establishes structural similarity to the B-type PDGF receptor. Proc. Natl. Acad. Sci. U.S.A. 86: 4917-4921.

Hough, R. B., A. Lengeling, V. Bedian, C. Lo and M. Bucan, 1998 Rump white inversion in the mouse disrupts dipeptidyl aminopeptidase-like protein 6 and causes dysregulation of Kit expression. Proc Natl Acad Sci USA 95: 13800-13805.

Marklund, S., M. Moller, K. Sandberg and L. Andersson, 1999 Close association between sequence polymorphism in the KIT gene and the roan coat color in horses. Mammalian Genome 10: 283-288.

Reinsch, N., H. Thomsen, N. Xu, M. Brink, C. Looft et al., 1999 A QTL for the degree of spotting in cattle shows synteny with the KIT locus on chromosome 6. J. Hered. 90: 629-634.

Rogel-Gaillard, C., A. Billault, N. Bourgeaux, M. Vaiman and P. Chardon, 1999 Characterisation and mapping of type C endogenous retroviral element in swine using a BAC library. Cytogenet and Cell Genet. 85: 273-278.

Spritz, R. A., K. M. Strunk, S. T. Lee, J. M. Lu-Kuo, D. C. Ward et al., 1994 A YAC contig spanning a cluster of human type m receptor protein tyrosine kinase genes (PDGFRA-KIT-KDR) in chromosome segment 4q12. Genomics 22: 431-436.

The invention claimed is:

1. A method of determining the KIT genotype of a pig which comprises:
   (i) obtaining a sample of pig nucleic acid; and
   (ii) analysing the nucleic acid obtained in (i) to identify the presence or absence of one or more copies of the duplication breakpoint, wherein the duplication break point comprises the sequence ATCTGAGAAGGCTA-CATACTGTATGATTCCAAGGGTCATGGCTTGAA AAAGAGACTGACC(SEQ ID NO: 18).

2. A method as claimed in claim 1, wherein (ii) is carried out using PCR techniques.

3. A method as claimed in claim 2, wherein the PCR techniques involve the use of one or more of the following pairs of primers:

```
5'-GTATTCACAGAGACTTGGCGGC-3'         (SEQ ID NO: 1)
and
5'-AAACCTGCAAGGAAAATCCTTCACGG-3';    (SEQ ID NO: 2)

5'-CTACCTTTGCCATACCATGCATTT-3'       (SEQ ID NO: 3)
and
5'-TTGCATGCCCTCTAATTACACAATT-3';     (SEQ ID NO: 4)

5'-CCACAATATACCTACAGAATTAC-3'        (SEQ ID NO: 5)
and
5'-AACCTGTGGATCAAATCTGGTC-3';        (SEQ ID NO: 6)

5'-GTTCAATCCAGCAATCACAACC-3'         (SEQ ID NO: 7)
and
5'-AACCTGTGGATCAAATCTGGTC-3';        (SEQ ID NO: 8)

5'-GTTCAATCCAGCAATCACAACC-3'         (SEQ ID NO: 9)
and
5'-TTTTAATCCTCTTAAGGACCAAC-3';       (SEQ ID NO: 10)

5'-TAAGTGAAAGAAGTCAATCTGAG-3'        (SEQ ID NO: 11)
and
5'-GGCAGTCATGTAACTATCACC-3'.         (SEQ ID NO: 12)
```

4. A method of determining the KIT genotype of a pig according to claim 1, which further comprises:
   (iii) analysing the nucleic acid obtained in (i) to quantify the percentage of splice variant copies of the KIT gene present.

5. A method as claimed in claim 4 wherein (iii) is carried out using minisequencing and/or pyrosequencing techniques.

6. A method as claimed in claim 4, which comprises determining the presence of at least one allele associated with at least one DNA marker linked either directly or indirectly to KIT.

7. A method as claimed in claim 1 which comprises determining the presence of at least one allele associated with at least one DNA marker linked either directly or indirectly to KIT.

8. A method as claimed in claim 7 wherein the DNA marker is a microsatellite.

9. A method as claimed in claim 8, wherein the DNA marker is S0086, S0017, Sw527, Swr750 or SW916.

10. A method as claimed in any one of claims 4, 7 or 6 which is used to determine coat colour genotype.

11. A method as claimed in any one of claims 4, 7 or 6 which is used for breed determination.

12. A method as claimed in any one of claims 4, 7 or 6 which is used to screen pigs to determine those more likely to produce large litters, and/or those less likely to produce larger litters.

13. A method as claimed in any one of claims 4, 7 or 6 which is used for selecting animals for preferred performance for other economic traits which vary according to KIT genotype.

14. A kit for determining the KIT genotype of a pig by analysing a sample of nucleic acid obtained from said pig to quantify the percentage of splice variant copies of the KIT gene present.

15. A kit as claimed in claim 14, including the primer 5'-TAATTACNTGGTCAAAGGAAAC-3', wherein N=inosine (SEQ ID NO: 17).

16. A kit for determining the KIT genotype of a pig by analysing a sample of nucleic acid obtained from said pig to identify the presence or absence of one or more copies of the duplication breakpoint.

17. A kit as claimed in claim 16, including one or more pairs of PCR primers.

18. A kit as claimed in claim 17, wherein the PCR primers are selected from any of the following:

```
5'-GTATTCACAGAGACTTGGCGGC-3'         (SEQ ID NO: 1)
and
5'-AAACCTGCAAGGAAAATCCTTCACGG-3';    (SEQ ID NO: 2)

5'-CTACCTTTGCCATACCATGCATTT-3'       (SEQ ID NO: 3)
and
5'-TTGCATGCCCTCTAATTACACAATT-3';     (SEQ ID NO: 4)

5'-CCACAATATACCTACAGAATTAC-3'        (SEQ ID NO: 5)
and
5'-AACCTGTGGATCAAATCTGGTC-3';        (SEQ ID NO: 6)

5'-GTTCAATCCAGCAATCACAACC-3'         (SEQ ID NO: 7)
and
5'-AACCTGTGGATCAAATCTGGTC-3';        (SEQ ID NO: 8)

5'-GTTCAATCCAGCAATCACAACC-3'         (SEQ ID NO: 9)
and
5'-TTTTAATCCTCTTAAGGACCAAC-3';       (SEQ ID NO: 10)

5'-TAAGTGAAAGAAGTCAATCTGAG-3'        (SEQ ID NO: 11)
and
5'-GGCAGTCATGTAACTATCACC-3'.         (SEQ ID NO: 12)
```

19. A method as claimed in claim 6, wherein the DNA marker is a microsatellite.

20. A method as claimed in claim 19, wherein the DNA marker is S0086, S0017, Sw527, Swr750 or SW916.

* * * * *